US011508063B2

(12) United States Patent
Buckler

(10) Patent No.: US 11,508,063 B2
(45) Date of Patent: Nov. 22, 2022

(54) NON-INVASIVE MEASUREMENT OF FIBROUS CAP THICKNESS

(71) Applicant: ELUCID BIOIMAGING INC., Boston, MA (US)

(72) Inventor: Andrew J. Buckler, Boston, MA (US)

(73) Assignee: ELUCID BIOIMAGING INC., Boston, MA (US)

(*) Notice: Subject to any disclaimer, the term of this patent is extended or adjusted under 35 U.S.C. 154(b) by 130 days.

(21) Appl. No.: 16/984,640

(22) Filed: Aug. 4, 2020

(65) Prior Publication Data

US 2021/0042918 A1 Feb. 11, 2021

Related U.S. Application Data

(60) Provisional application No. 62/882,881, filed on Aug. 5, 2019.

(51) Int. Cl.
*G06T 7/00* (2017.01)
*G06T 7/11* (2017.01)
(Continued)

(52) U.S. Cl.
CPC ........ *G06T 7/0012* (2013.01); *A61B 5/02007* (2013.01); *A61B 6/504* (2013.01);
(Continued)

(58) Field of Classification Search
CPC ............. G06T 7/0012; G06T 7/11; G06T 2207/30101; G06T 2207/10081;
(Continued)

(56) References Cited

U.S. PATENT DOCUMENTS 6,108,635 A 8/2000 Herren et al.
7,127,095 B2 10/2006 Fakhri et al.
(Continued)

FOREIGN PATENT DOCUMENTS

WO WO2014049574 4/2014
WO WO 2015058151 4/2015
WO WO2019016309 1/2019

OTHER PUBLICATIONS

Nadkarni et al., "Measurement of fibrous cap thickness in atherosclerotic plaques be spatiotemporal analysis of laser speckle images", Journal of Biomedical Optics, Mar. 2006 (Year: 2006).*
(Continued)

*Primary Examiner* — Vu Le
*Assistant Examiner* — Julius Chai
(74) *Attorney, Agent, or Firm* — Pearl Cohen Zedek Latzer Baratz LLP

(57) ABSTRACT

A system including a hierarchical analytics framework that can utilize a first set of machine learned algorithms to identify and quantify a set of biological properties utilizing medical imaging data is provided. System can segment the medical imaging data based on the quantified biological properties to delineate existence of perivascular adipose tissue. The system can also segment the medical imaging data based on the quantified biological properties to determine a lumen boundary and/or determine a cap thickness based on a minimum distance between the lumen boundary and LRNC regions.

8 Claims, 10 Drawing Sheets

(51) Int. Cl.
*A61B 6/00* (2006.01)
*A61B 8/08* (2006.01)
*A61B 5/02* (2006.01)

(52) U.S. Cl.
CPC .............. *A61B 8/0891* (2013.01); *G06T 7/11* (2017.01); *G06T 2207/30101* (2013.01)

(58) Field of Classification Search
CPC ...... G06T 2207/30048; A61B 5/02007; A61B 6/504; A61B 6/5217; A61B 6/05; A61B 8/0891
See application file for complete search history.

(56) References Cited

U.S. PATENT DOCUMENTS

| | | | |
|---|---|---|---|
| 7,519,211 B2 | 4/2009 | Fakhri et al. | |
| 8,157,742 B2 | 4/2012 | Taylor | |
| 8,175,355 B2 | 5/2012 | Fakhri et al. | |
| 8,249,815 B2 | 8/2012 | Taylor | |
| 8,311,747 B2 | 11/2012 | Taylor | |
| 8,311,748 B2 | 11/2012 | Taylor et al. | |
| 8,311,750 B2 | 11/2012 | Taylor | |
| 8,315,812 B2 | 11/2012 | Taylor | |
| 8,315,813 B2 | 11/2012 | Taylor et al. | |
| 8,315,814 B2 | 11/2012 | Taylor et al. | |
| 8,321,150 B2 | 11/2012 | Taylor | |
| 8,374,689 B2 | 2/2013 | Gopinathan et al. | |
| 8,386,188 B2 | 2/2013 | Taylor et al. | |
| 8,496,594 B2 | 7/2013 | Taylor et al. | |
| 8,523,779 B2 | 9/2013 | Taylor et al. | |
| 8,548,778 B1 | 10/2013 | Hart et al. | |
| 8,553,832 B2 | 10/2013 | Camus et al. | |
| 8,554,490 B2 | 10/2013 | Tang et al. | |
| 8,594,950 B2 | 11/2013 | Taylor | |
| 8,606,530 B2 | 12/2013 | Taylor | |
| 8,630,812 B2 | 1/2014 | Taylor | |
| 8,706,457 B2 | 4/2014 | Hart et al. | |
| 8,734,356 B2 | 5/2014 | Taylor | |
| 8,734,357 B2 | 5/2014 | Taylor | |
| 8,768,669 B1 | 7/2014 | Hart et al. | |
| 8,768,670 B1 | 7/2014 | Hart et al. | |
| 8,812,245 B2 | 8/2014 | Taylor | |
| 8,812,246 B2 | 8/2014 | Taylor | |
| 8,824,752 B1 | 9/2014 | Fonte et al. | |
| 8,825,151 B2 | 9/2014 | Gopinathan et al. | |
| 8,831,314 B1 | 9/2014 | Fonte et al. | |
| 8,831,315 B1 | 9/2014 | Fonte et al. | |
| 8,855,984 B2 | 10/2014 | Hart et al. | |
| 8,861,820 B2 | 10/2014 | Fonte et al. | |
| 8,914,264 B1 | 12/2014 | Hart et al. | |
| 8,970,578 B2 | 3/2015 | Voros et al. | |
| 8,977,339 B1 | 3/2015 | Wu et al. | |
| 9,002,690 B2 | 4/2015 | Hart et al. | |
| 9,008,405 B2 | 4/2015 | Fonte et al. | |
| 9,042,613 B2 | 5/2015 | Spilker et al. | |
| 9,043,190 B2 | 5/2015 | Grady et al. | |
| 9,063,634 B2 | 6/2015 | Hart et al. | |
| 9,063,635 B2 | 6/2015 | Hart et al. | |
| 9,078,564 B2 | 7/2015 | Taylor | |
| 9,081,882 B2 | 7/2015 | Taylor | |
| 9,087,147 B1 | 7/2015 | Fonte | |
| 9,119,540 B2 | 9/2015 | Sharma et al. | |
| 9,149,197 B2 | 10/2015 | Taylor | |
| 9,152,757 B2 | 10/2015 | Taylor | |
| 9,155,512 B2 | 10/2015 | Choi et al. | |
| 9,167,974 B2 | 10/2015 | Taylor | |
| 9,168,012 B2 | 10/2015 | Hart et al. | |
| 9,189,600 B2 | 11/2015 | Spilker et al. | |
| 9,195,801 B1 | 11/2015 | Sankaran et al. | |
| 9,202,010 B2 | 12/2015 | Taylor et al. | |
| 9,220,418 B2 | 12/2015 | Choi et al. | |
| 9,220,419 B2 | 12/2015 | Choi et al. | |
| 9,226,672 B2 | 1/2016 | Taylor | |
| 9,235,679 B2 | 1/2016 | Taylor | |
| 9,239,905 B1 | 1/2016 | Sankaran et al. | |
| 9,247,918 B2 | 2/2016 | Sharma et al. | |
| 9,262,581 B2 | 2/2016 | Kim et al. | |
| 9,265,473 B2 | 2/2016 | Mittal et al. | |
| 9,268,902 B2 | 2/2016 | Taylor et al. | |
| 9,271,657 B2 | 3/2016 | Taylor | |
| 9,280,639 B2 | 3/2016 | Sankaran et al. | |
| 9,292,659 B1 | 3/2016 | Grady et al. | |
| 9,320,487 B2 | 4/2016 | Mittal et al. | |
| 9,336,354 B1 | 5/2016 | Sankaran et al. | |
| 9,339,200 B2 | 5/2016 | Fonte | |
| 9,349,178 B1 | 5/2016 | Itu et al. | |
| 9,386,933 B2 | 5/2016 | Grady et al. | |
| 9,390,224 B2 | 7/2016 | Choi et al. | |
| 9,390,232 B2 | 7/2016 | Taylor et al. | |
| 9,405,886 B2 | 8/2016 | Taylor et al. | |
| 9,424,395 B2 | 8/2016 | Sankaran et al. | |
| 9,449,145 B2 | 9/2016 | Sankaran et al. | |
| 9,449,146 B2 | 9/2016 | Spilker et al. | |
| 9,449,147 B2 | 9/2016 | Taylor | |
| 9,471,999 B2 | 10/2016 | Ishi et al. | |
| 9,501,622 B2 | 11/2016 | Sankaran et al. | |
| 9,517,040 B2 | 12/2016 | Hart et al. | |
| 9,538,925 B2 | 1/2017 | Sharma et al. | |
| 9,572,495 B2 * | 2/2017 | Schmitt | A61B 5/02007 |
| 9,585,623 B2 | 3/2017 | Fonte et al. | |
| 9,585,723 B2 | 3/2017 | Taylor | |
| 9,595,089 B2 | 3/2017 | Itu et al. | |
| 9,607,130 B2 | 3/2017 | Grady et al. | |
| 9,607,386 B2 | 3/2017 | Grady et al. | |
| 9,649,171 B2 | 3/2017 | Sankaran et al. | |
| 9,613,186 B2 | 4/2017 | Fonte | |
| 9,629,563 B2 | 4/2017 | Sharma et al. | |
| 9,633,454 B2 | 4/2017 | Lauritsch et al. | |
| 9,668,700 B2 | 6/2017 | Taylor | |
| 9,672,615 B2 | 6/2017 | Fonte et al. | |
| 9,675,301 B2 | 6/2017 | Fonte et al. | |
| 9,679,374 B2 | 6/2017 | Choi et al. | |
| 9,697,330 B2 | 7/2017 | Taylor | |
| 9,700,219 B2 | 7/2017 | Sharma et al. | |
| 9,706,925 B2 | 7/2017 | Taylor | |
| 9,737,276 B2 | 8/2017 | Mittal et al. | |
| 9,743,835 B2 | 8/2017 | Taylor | |
| 9,747,525 B2 | 8/2017 | Sauer et al. | |
| 9,754,082 B2 | 9/2017 | Taylor et al. | |
| 9,757,073 B2 | 9/2017 | Goshen et al. | |
| 9,761,048 B2 | 9/2017 | Igarashi | |
| 9,770,303 B2 | 9/2017 | Choi et al. | |
| 9,773,219 B2 | 9/2017 | Sankaran et al. | |
| 9,785,746 B2 | 10/2017 | Fonte et al. | |
| 9,785,748 B2 | 10/2017 | Koo et al. | |
| 9,786,068 B2 | 10/2017 | Ishi et al. | |
| 9,788,807 B2 | 10/2017 | Schmitt et al. | |
| 9,801,689 B2 | 10/2017 | Taylor | |
| 9,805,168 B2 | 10/2017 | Sankaran et al. | |
| 9,805,463 B2 | 10/2017 | Choi et al. | |
| 9,594,876 B2 | 12/2017 | Sankaran et al. | |
| 9,836,840 B2 | 12/2017 | Fonte et al. | |
| 9,839,399 B2 | 12/2017 | Fonte et al. | |
| 9,839,483 B2 | 12/2017 | Sankaran et al. | |
| 9,839,484 B2 | 12/2017 | Taylor | |
| 9,842,401 B2 | 12/2017 | Prevrhal et al. | |
| 9,855,105 B2 | 1/2018 | Taylor | |
| 9,858,387 B2 | 1/2018 | Lavi et al. | |
| 9,861,284 B2 | 1/2018 | Taylor | |
| 9,864,840 B2 | 1/2018 | Grady et al. | |
| 9,877,657 B2 | 1/2018 | Igarashi | |
| 9,888,968 B2 | 2/2018 | Sauer et al. | |
| 9,888,971 B2 | 2/2018 | Taylor | |
| 9,891,044 B2 | 2/2018 | Tu et al. | |
| 9,913,616 B2 | 3/2018 | Fonte et al. | |
| 9,918,690 B2 | 3/2018 | Itu et al. | |
| 9,924,869 B2 | 3/2018 | Kim et al. | |
| 9,928,593 B2 | 3/2018 | Ooga et al. | |
| 10,092,247 B2 | 3/2018 | Taylor | |
| 9,940,736 B2 | 4/2018 | Ishi et al. | |
| 9,943,233 B2 | 4/2018 | Lavi et al. | |
| 9,949,650 B2 | 4/2018 | Edic et al. | |
| 9,965,891 B2 | 5/2018 | Grady et al. | |

(56) References Cited

U.S. PATENT DOCUMENTS

| | | | |
|---|---|---|---|
| 9,974,454 B2 | 5/2018 | Sharma et al. | |
| 9,974,508 B2 | 5/2018 | Kassab et al. | |
| 9,974,616 B2 | 5/2018 | Grady et al. | |
| 9,977,869 B2 | 5/2018 | Lavi et al. | |
| 9,984,465 B1 | 5/2018 | Ma et al. | |
| 9,993,303 B2 | 6/2018 | Sankaran et al. | |
| 9,999,361 B2 | 6/2018 | Sharma et al. | |
| 10,002,419 B2 | 6/2018 | Rapaka et al. | |
| 10,007,762 B2 | 6/2018 | Grady et al. | |
| 10,010,255 B2 | 7/2018 | Fonte et al. | |
| 10,034,614 B2 | 7/2018 | Edic et al. | |
| 10,052,031 B2 | 8/2018 | Sharma et al. | |
| 10,052,032 B2 | 8/2018 | Grass et al. | |
| 10,052,158 B2 | 8/2018 | Taylor | |
| 10,080,613 B2 | 9/2018 | Taylor | |
| 10,080,614 B2 | 9/2018 | Taylor | |
| 10,092,360 B2 | 10/2018 | Taylor | |
| 10,096,104 B2 | 10/2018 | Choi et al. | |
| 2002/0103776 A1 | 8/2002 | Bella et al. | |
| 2003/0105638 A1 | 6/2003 | Taira | |
| 2005/0043614 A1* | 2/2005 | Huizenga | A61B 5/055 600/427 |
| 2005/0118632 A1 | 6/2005 | Chen | |
| 2006/0242288 A1 | 10/2006 | Masurkar | |
| 2007/0130206 A1 | 6/2007 | Zhou et al. | |
| 2007/0208516 A1 | 9/2007 | Kutsyy et al. | |
| 2007/0260141 A1 | 11/2007 | Margolis | |
| 2008/0027695 A1 | 1/2008 | Balgi et al. | |
| 2008/0201280 A1 | 8/2008 | Martin et al. | |
| 2009/0171871 A1 | 7/2009 | Zhang et al. | |
| 2009/0258925 A1 | 10/2009 | Wahlestdt | |
| 2009/0259459 A1 | 10/2009 | Ceusters et al. | |
| 2009/0324126 A1 | 12/2009 | Zitnick | |
| 2010/0070448 A1 | 3/2010 | Omoigui | |
| 2010/0262545 A1 | 10/2010 | Herlitz | |
| 2011/0026798 A1 | 2/2011 | Madabhushi | |
| 2011/0027181 A1 | 2/2011 | Amodei et al. | |
| 2011/0245650 A1* | 10/2011 | Kerwin | G06T 7/0012 600/407 |
| 2012/0278060 A1 | 11/2012 | Cancedda | |
| 2013/0275094 A1 | 10/2013 | Ortoleva | |
| 2014/0126770 A1 | 5/2014 | Odessky et al. | |
| 2014/0276121 A1 | 9/2014 | Kassab | |
| 2014/0365239 A1 | 12/2014 | Sadeghi | |
| 2015/0154275 A1 | 6/2015 | Senart et al. | |
| 2015/0234921 A1 | 8/2015 | Li | |
| 2015/0324527 A1 | 11/2015 | Siegal et al. | |
| 2016/0203599 A1* | 7/2016 | Gillies | A61B 5/7271 382/132 |
| 2016/0310018 A1 | 10/2016 | Fonte | |
| 2016/0314580 A1 | 10/2016 | Lloyd | |
| 2016/0326588 A1 | 11/2016 | Beier | |
| 2016/0364630 A1 | 12/2016 | Reicher et al. | |
| 2017/0046839 A1* | 2/2017 | Paik | G06K 9/6296 |
| 2017/0245829 A1* | 8/2017 | Nair | G16H 50/20 |
| 2017/0265832 A1* | 9/2017 | Antoniades | G16H 50/30 |
| 2017/0337343 A1* | 11/2017 | Kakadiaris | G16H 50/20 |
| 2017/0358079 A1 | 12/2017 | Gillies | |
| 2018/0253591 A1 | 9/2018 | Madabhushi | |
| 2018/0330477 A1 | 11/2018 | Paik et al. | |
| 2019/0244347 A1 | 8/2019 | Buckler et al. | |
| 2019/0247050 A1* | 8/2019 | Goldsmith | A61F 2/82 |
| 2019/0287276 A1* | 9/2019 | Antoniades | A61B 6/504 |
| 2020/0126672 A1* | 4/2020 | Rabbat | A61B 5/7278 |
| 2020/0226749 A1* | 7/2020 | Freiman | G16H 50/30 |
| 2020/0237329 A1* | 7/2020 | Min | A61B 6/5217 |

OTHER PUBLICATIONS

Antoniades et al. State-of-the-art review article. Atherosclerosis affecting fat: What can we learn by imaging perivascular adipose tissue?, Journal of Cardiovascular Computed Tomography 13(2019) 288-296.

Nadkarni et al., Measurement of fibrous cap thickness in atherosclerotic plaques by spatiotemporal analysis of laser speckle images. Journal of Biomedical Optics; 11(2):Mar. 1, 2006 (Mar. 1, 2006), 16 pgs.

PCT Search Report for appl. No. PCT/US2020/044845 dated Oct. 26, 2020.

Castellano et al. "Texture analysis of medical images," Clinical Radiology, Dec. 1, 2004 (Dec. 1, 2004) vol. 59.

Choi et al. "Multiscale image segmentation using wavelet-domain hidden Markov models" IEEE Trans Image Process, Sep. 1, 2001 (Sep. 1, 2001), vol. 10.

Reedy et al. "Confidence guided enhancing brain tumor segmentation in multi-parametric MRI" Proceedings of the 12$^{th}$ International Conference on Medical Image Computing and Computer-Assisted Intervention, MICCAI 2009, held in London, UK, Sep. 20, 2009.

Khan et al., "Robust atlas-based brain segmentation using multi-structure confidence-weighted registration" Proceedings of the 12th International Conference on Medical Image Computing, Sep. 20, 2009.

Ariff et al. "Carotid Artery Hemodynamics: Observing Patient-specific Changes with Amlodipine and Lisinopril by Using MRI Imaging Computation Fluid Dynamics." Radiol. 257.3(2010):662-669.

Bourque et al. "Usefulness of Cardiovascular Magnetic Resonance Imaging of the Superficial Femoral Artery for Screening Patients with Diabetes Mellitus for Artherosclerosis." Am. J. Cardiol. 110. 1(2012):50-56.

Buckler et al. "A Collaborative Enterprise for Multi-Stakeholder Participation in the Advancement of Quantitative Imaging." Radiol. 258.3(2011):906-914.

Buckler et al. "Data Sets for the Qualification of CT as a Quantitative Imaging Biomarker in Lung Cancer." Optics Exp.18. 14(2010):16.

Buckler et al. "Data Sets for the Qualification of Volumetric CT as a Quantitative Imaging Biomarker in Lung Cancer." Optics Exp. 18.14(2010):15267-15282.

Buckler et al. "Quantitative Imaging Test Approval and Biomarker Qualification: Interrelated but Distinct Activities." Radiol. 259. 3(2011):875-884.

Buckler et al. "Standardization of Quantitative Imaging: The Time is Right and 18F-FDG PET/CT is a Good Place to Start." J. Nuclear Med. 52.2(2011):171-172.

Buckler et al. "The Use of Volumetric CT as an Imaging Biomarker in Lung Cancer." Academic Radiol. 17.1(2010):100-106.

Buckler et al. "Volumetric CT in Lung Cancer: An Example for the Qualification of Imaging as a Biomarker." Academic Radiol. 17.1(2010):107-115.

Buyse et al. "The Validation of Surrogate Endpoints in Meta-Analysis of Randomized Experiments." Biostat. 1 (2000):1-1.

Chan et al. "Active Contours without Edges." IEEE Trans. Image Process. 10.2(2001):266-277.

De Weert et al. "In Vivo Characterization and Quantification of Atherosclerotic Carotid Plaque Components with Multidetector Computed Tomography and Histopathlogical Correlation." Arterioscler. Thromb. Vase. Biol. 26.10 2006):2366-2372.

Fleming. "Surrogate Endpoints and FDA's Accelerated Approval Process." Health Affairs. 24.1{2005):67-78.

Freedman et al. "Statistical Validation of Intermediate Endpoints for Chronic Diseases." Stat. Med. 11(1992):167-178.

Fuleihan et al. "Reproducibility of DXA Absorptiometry: A Model for Bone Loss Estimates." J. Bone Miner. Res. 10.74 (1995):1004-1014.

Horie et al. "Assessment of Carotid Plaque Stability Based on Dynamic Enhancement Pattern in Plaque Components with Multidetector CT Angiography." Stroke. 43.2{2012):393-398.

Irace et al. "Human Common Carotid Wall Shear Stress as a Function of Age and Gender: A 12-year Follow-up Study." AGE. 34.6(2012):1553-1562.

Jaffe, "Measures of Response: RECIST, WHO, and New Alternatives." J.Clin. Oncol. 24.20(2006):3245-3251.

Katz, "Biomarkers and Surrogate Markers: An FDA Perspective." NeuroRx. 1.2(2004):189-195.

(56) References Cited

OTHER PUBLICATIONS

Kerwin et al. "MRI of Carotid Artherosclerosis." Am. J. Roentgenol. 200.3(2013):W304-W313.
Kim et al. "A Curve Evolution-based variational approach to Simultaneous Image Restoration and Segmentation." EEE Int. Conf. Image Proc. (2002):1-109.
Lathia et al. "The Value, Qualification, and Regulatory Use of Surrogate End Points in Drug Development." Clin Pharmacol. Therapeutics. 86.1(2009):32-43.
Mozley et al. "Change in Lung Tumor Volume as a Biomarker of Treatment Response: A Critical Review of the Evidence." Ann. Oncol. 21.9(2010):1751-1755.
Phinikaridou et al. "Regions of Low Endothelial Shear Stress Colocalize with Positive Vascular Remodeling and Atherosclerotic Plaque Disruption: An in vivo Magnetic Resonance Imaging Study." Circ. Cardiovasc. Imaging. 6.2 (2013):302-310.
Prentice, "Surrogate Endpoints in Clinical Trials: Definition and Operational Criteria." Stat. Med. 9(1989):431-440.
Sargent et al. "Validation of Novel Imaging Methodologies for Use as Cancer Clinical Trial End-points." Eur. J. Dis. 45 ('2009):290-299.
Sui et al. "Assessment of Wall Shear Stress in the Common Carotid Artery of Healthy Subjects Using 3.0-Tesla Magentic Resonance." Acta Radiologica. 49.4(2008):442-449.
Ten Kate et al. "Noninvasive Imaging of the Vulnerable Atherosclerotic Plaque." Current Problems Cardiol. 35.11(2010):556-591.
Van Klavern et al."Management of Lung Nodules Detected by Volume CT Scanning." New Engl. J. Med. 361 (2009):23.
Varma et al. "Coronary Vessel Wall Contrast Enhancement Imaging as a Potential Direct Marker of Coronary Involvement: Integration of Findings from CAD and SLE Patients." JACC Cardiovasc. Imaging. 7.8(2014):762-770.
Wintermark et al. "Carotid Plaque CT Imaging in Stroke and Non-Stroke Patients." Ann. Neurol. 64.2(2008):149-157.
Wintermark et al. "High-Resolution CT Imaging of Carotid Artery Atherosclerotic Plaques." Am. J. Neuroradiol. 29.5 (2008):875-882.
Wong et al. "Imaging in Drug Discovery, Preclinical, and Early Clinical Development." J. Nuclear Med. 49.6 (2008):26N-28N.
Woodcock et al. "The FDA Critical Path Initiative and its Influence on New Drug Development." Annu. Rev. Med. 59 (2008):1-12.
Zavodni et al. "Carotid Artery Plaque Morphology and Composition in Relation to Incident Cardiovascular Events: The Multi-Ethnic Study of Atherosclerosis (MESA)." Radiol. 271.2(2014):361-389.
Zhao et al. "Evaluating Variability in Tumor Measurements from Same-Day Repeat CT Scans of Patients with Non-Small Cell Lung Cancer." Radiol. 252.1(2009):263-272.
Aerts,H. J.W.L., et al., Decoding tumour phenotype by noninvasive imaging using a quantitative radiomics approach. Nat Commun, 2014. 5.
Ahmadi, A., et al., Association of Coronary Stenosis and Plaque Morphology With Fractional Flow Reserve and Outcomes. JAMA Cardiol, 2016.1(3): p. 350-7.
Ahmadi, A., et al., Lesion-Specific and Vessel-Related Determinants of Fractional Flow Reserve Beyond Coronary Artery Stenosis. JACC Cardiovasc Imaging,2018. 11(4): p. 521-530.
Albuquerque, L C , et al., Intraplaque hemorrhage assessed by high-resolution magnetic resonance imaging and C-reactive protein in carotid atherosclerosis. Journal of Vascular Surgery, 2007.46(6): p. 1130-1137.
Alimohammadi, M., et al., Development of a Patient-Specific Multi-Scale Model to Understand Atherosclerosis and Calcification Locations: Comparison with In vivo Data in an Aortic Dissection Front Physiol, 2016. 7: p. 23.
Aoki, T., et al., Peripheral Lung Adenocarcinoma: Correlation of Thin-Section CT Findings with Histologic Prognostic Factors and Survival 1. Radiology, 2001.220(3): p. 803-809.
Atkinson,A.J., et al., Biomarkers and surrogate endpoints: Preferred definitions and conceptual framework*. Clinical Pharmacology & Therapeutics, 2001. 69(3): p. 89-95.

Bittencourt, M.S., et al., Prognostic Value of Nonobstructive and Obstructive Coronary Artery Disease Detected by Coronary Computed Tomography Angiography to Identify Cardiovascular Events. Circulation: Cardiovascular Imaging, 2014.7(2): p. 282-291.
Buckler,A., et al., A Novel Knowledge Representation Framework for the Statistical Validation of Quantitative Imaging Biomarkers. Journal of Digital Imaging, 2013. 26(4): p. 614-629.
Buckler, A.J., et al., Quantitative imaging biomarker ontology (QIBO) for knowledge representation of biomedical imaging biomarkers. Journal of digital imaging : the official journal of the Society for Computer Applications in Radiology, 2013. 26(4): p. 630-41.
Buckler, A.J., et al., Quantitative imaging test approval and biomarker qualification: interrelated but distinct activities. Radiology, 2011. 259(3): p. 875-84.
Cai, J., et al., In vivo quantitative measurement of intact fibrous cap and lipid-rich necrotic core size in atherosclerotic carotid plaque: comparison of high-resolution, contrast-enhanced magnetic resonance imaging and histology. Circulation, 2005. 112(22): p. 3437-14.
Chan, T.F. and L.A. Vese, Active contours without edges. IEEE Trans Image Process,2001. 10(2): p. 266-77.
Coenen, A., et al., Diagnostic accuracy of a machine-learning approach to coronary computed tomographic angiography-based fractional flow reserve: result from the Machine consortium. Circulation: Cardiovascular Imaging, 2018. 11(6): p. e007217.
De Bono, B., et al., The Open Physiology workflow: modeling processes over physiology circuit boards of interoperable tissue units Front Physiol, 2015. 6: p. 24.
De Graaf, M., et al., Automatic quantification and characterization of coronary atherosclerosis with computed tomography coronary angiography: cross-correlation with intravascular ultrasound virtual histology. Int J Cardiovasc Imaging, 2013. 29(5): p. 1177-1190.
DeMarco, J.K. and J. Huston, Imaging of high-risk carotid artery plaques: current status and future directions Neurosurgical Focus, 2014. 36(1): p. E1.
Diaz-Zamudio, M., et al., Automated Quantitative Plaque Burden from Coronary CT Angiography Noninvasively Predicts Hemodynamic Significance by using Fractional Flow Reserve in Intermediate Coronary Lesions. Radiology, 2015.276(2): p. 408-15.
Dong, L., et al., Carotid Artery Atherosclerosis: Effect of Intensive Lipid Therapy on the Vasa Vasorum—Evaluation by Using Dynamic Contrast-enhanced MR Imaging. Radiology, 2011.260(1): p. 224-231.
Fiilardi,V., Carotid artery stenosis near a bifurcation investigated by fluid dynamic analyses. The Neuroradiology Journal, 2013. 26(4):p. 439-453.
Fleming,T.R. and D.L. DeMets, Surrogate end points in clinical trials:are we being misled? Ann Intern Med, 1996. 125 (7): p. 605-13.
Freimuth, R.R.,et al., Life sciences domain analysis model. J Am Med Inform Assoc,2012. 19(6): p. 1095-102.
Fujimoto,S.,et al., A novel method for non-invasive plaque morphology analysis by coronary computed tomography angiography. Int J Cardiovasc Imaging, 2014. 30(7): p. 1373-1382.
Gaston A. Rodriguez-Granillo, Patricia Carrascosa, Nico Bruining, and a.H.M.G.-G. Ron Waksman, Defining the non-vulnerable and vulnerable patients with computed tomography coronary angiography: evaluation of atherosclerotic plaque burden and composition. European Heart Journal—Cardiovascular Imaging, 2016. 2016(17): p. 481-491.
Gevaert, O., et al., Non-small cell lung cancer: identifying prognostic imaging biomarkers by leveraging public gene expression microarray data—methods and preliminary results Radiology, 2012 264(2): p. 387-396.
Ghazalpour, A., et al., Thematic review series: The pathogenesis of atherosclerosis. Toward a biological network for atherosclerosis J Lipid Res, 2004 45(10): p. 1793-805.
Gupta, A., et al., Carotid Plaque MRI and Stroke Risk A Systematic Review and Meta-analysis. Stroke, 2013.44(11): p. 3071-3077.
Gupta, A., et al., Detection of Symptomatic Carotid Plaque Using Source Data from MR and CT Angiography: A Correlative Study Cerebrovasc Dis, 2015. 39(3-4): p. 151-61.

(56) References Cited

OTHER PUBLICATIONS

Gupta, A., et al., Intraplaque high-intensity signal on 3D time-of-flight MR angiography is strongly associated with symptomatic carotid artery stenosis. American Journal of Neuroradiology, 2014. 35(3): p. 557-561.
Hecht, H.S., Coronary artery calcium scanning: past, present, and future. JACC Cardiovasc Imaging, 2015. 8:p. 579-596.
Hecht,H.S., J. Narula, and W.F. Fearon, Fractional Flow Reserve and Coronary Computed Tomographic Angiography, A Review and Critical Analysis. Circ Res, 2016.119(2): p. 300-16.
Helft, G., et al., Progression and regression of atherosclerotic lesions: monitoring with serial noninvasive magnetic resonance imaging Circulation, 2002. 105(8): p. 993-8.
Inoue, K., et al., Serial Coronary CT Angiography-Verified Changes in Plaque Characteristics as an End Point: Evaluation of Effect of Statin Intervention. JACC: Cardiovascular Imaging, 2010. 3(7): p. 691-698.
Krizhevsky, A.I. Sutskever, and G.E. Hinton. Imagenet classification with deep convolutional neural networks. In Advances in neural information processing systems 2012.
Lobatto, ME., et al., Multimodal Clinical Imaging To Longitudinally Assess a Nanomedical Anti-Inflammatory Treatment in Experimental Atherosclerosis. Molecular Pharmaceutics, 2010. 7(6): p. 2020-2029.
Ma, X., et al Volumes Learned: It Takes More Than Size to "Size Up" Pulmonary Lesions. Acad Radiol, 2016. 23(9):p. 1190-8.
Melander, O., et al., Novel and conventional biomarkers for prediction of incident cardiovascular events in the community. JAMA: the journal of the American Medical Association, 2009. 302(1): p. 49-57.
Miao, C., et al., The Association of Pericardial Fat with Coronary Artery Plaque Index at MR Imaging: The Multi-Ethnic Study of Atherosclerosis (MESA). Radiology, 2011.261(1): p. 109-115.
Mono, M.L., et al., Plaque Characteristics of Asymptomatic Carotid Stenosis and Risk of Stroke. Cerebrovascular Diseases, 2012. 34(5-6):p. 343-350.
Narula, J., et al., Histopathologic characteristics of atherosclerotic coronary disease and implications of the findings for the invasive and noninvasive detection of vulnerable plaques. Journal of the American College of Cardiology, 2013. 61(i0): p. 1041-1051.
Naylor, A.R., Identifying the high-risk carotid plaque. The Journal of Cardiovascular Surgery, 2014. 55(2): p. 11-20.
Perera ,R. and P. Nand, Recent Advances in Natural Language Generation: A Survey and Classification of the Empirical Literature. vol. 36.2017. 1-31.
Prentice, R.L., Surrogate endpoints in clinical trials: definition and operational criteria. Statistics in medicine, 1989. 8 (4): p. 431-440.
Prescott, J., Quantitative Imaging Biomarkers: The Application of Advanced Image Processing and Analysis to Clinical and Preclinical Decision Making Journal of Digital Imaging, 2013. 26(1):p. 97-108.
Reddy et al. "Confidence guided enhancing brain tumor segmentation in multi-parametric MRI" Proceedings of the 12th International Conference on Medical Image Computing and Computer-Assisted Intervention, MICCAI 2009, held in London, UK, Sep. 20, 2009.
Saba, L., et al., Carotid Artery Plaque Characterization Using CT Multienergy Imaging American Journal of Neuroradiology, 2013 34(4): p. 855-859.
Sadot, A., et al., Toward verified biological models. IEEE/ACM Trans Comput Biol Bioinform, 2008. 5(2): p. 223-34.
Sargent, D., et al., Validation of novel imaging methodologies for use as cancer clinical trial end-points. European Journal of Cancer, 2009.45(2): p. 290-299.
Stary, H.C., et al., A definition of advanced types of atherosclerotic lesions and a histological classification of atherosclerosis A report from the Committee on Vascular Lesions of the Council on Arteriosclerosis, American Heart Association. Circulation,1995. 92(5):p. 1355-1374.
Stary, H.C., Natural history and histological classification of atherosclerotic lesions: an update. Arterioscler Thromb Vase Biol, 2000.20(5):p. 1177-8.
Van't Klooster ,R., et al., Visualization of Local Changes in Vessel Wall Morphology and Plaque Progression in Serial Carotid Artery Magnetic Resonance Imaging. Stroke, 2014.45(8): p. e160-e163.
Virmani, R., et al., Pathology of the Vulnerable Plaque. JACC,2006. 47(8): p. C13-8.
Voros, S., et al., Coronary Atherosclerosis Imaging by Coronary CT Angiography. JACC Cardiovasc Imaging, 2011.4 (5): p. 537-48.
William B. Kerr et al. "A Methodology and Metric for Quantitative Analysis and Parameter Optimization of Unsupervised, Multi-Region Image Segmentation", Proceeding of the 8th IASTED International Conference on Signal and Image Processing, Aug. 14, 2006, pp. 243-248.
Rolim S. Fernandes, Veronica et al. Atherosclerosis imaging and heart failure, Heart Failure Reviews, Kluwer Academic Publishers, BO, vol. 11, No. 4, Dec. 1, 2006, pp. 279-288.
Toussaint J.F. MRI characterization of atherosclerotic arteries: diagnosis of plaque rupture, Database Medline, Online, US National Library of Medicine (NLM) Bethesda MD, US, Dec. 2002, XP002807101, database accession No. NLM12538939, Abstract.
European Search Report for Appl. No. 20851022.2 dated Jul. 29, 2022.

\* cited by examiner

NON-INVASIVE MEASUREMENT OF FIBROUS CAP THICKNESS

CROSS REFERENCE TO RELATED APPLICATIONS

This application claims the benefit of and priority to U.S. provisional patent application No. 62/882,881, filed on Aug. 5, 2019, the entire contents of which are incorporated herein by reference in its entirety and owned by the assignee of the instant application.

GOVERNMENT RIGHTS

This work was supported in part by NIH award ID HL 126224. The government may have certain rights in the invention.

FIELD OF THE INVENTION

The invention relates to computer-aided phenotyping (CAP) of disease which can include applying computerized image analysis and/or data fusion algorithms to patient data. In particular, the invention relates to quantitative imaging and analytics for elucidating the disease process of atherosclerosis, including delineating perivascular adipose tissue and/or determining the thickness of tissues between the lipid-rich necrotic core (LRNC) and the lumen ("cap thickness") of a blood vessel.

BACKGROUND OF THE INVENTION

Atherosclerosis can be life threatening, particularly in aging populations, but even among the relatively young. Current methods for diagnosing atherosclerosis, for example, the use of blood markers e.g., cholesterol levels) and/or determining the degree to which the lumen is narrowed (stenosis) are limited, and thus can result in suboptimal treatment decisions (e.g., to perform or not to perform surgeries, or prescribe intensive medical therapy). For example, many vascular surgeries do not benefit the patient, some that need surgeries don't get them, and many could be effectively treated with drugs but may not be prescribed them.

Current tools can analyze a blood vessel lumen, but this can be insufficient for truly diagnosing atherosclerosis, as atherosclerosis is a disease of the vessel wall, rather than the blood or the channel through which it flows. High rates of misclassified risk level, inability to assess likely response to drug therapy, and/or inability to measure response to drugs can occur.

Currently, radiological imaging can be used as a non-invasive and safe method for locating disease origin. Current medical imaging tools can include computed tomography (CT, including single energy, multi-energy, or spectral CT), magnetic resonance imaging (MR, MRA, DCE-MRI, or multi-contrast MRI), ultrasound (b-mode or intravascular US), and targeted contrast agent approaches with various imaging modalities.

Enhanced imaging techniques have made medical imaging an essential component of patient care. Imaging can be valuable because it can provide spatially and temporally localized anatomic and/or functional information, using non- or minimally invasive methods. However, techniques to deal with increasing resolution can be desired, both to exploit patterns and/or signatures in the data typically not readily assessed with the human eye, as well as to, for example, manage a large magnitude of data to efficiently integrate it into the clinical workflow. With newer high-resolution imaging techniques, unaided, the radiologist can "drown" in data. Therefore, in order to, for example, integrate quantitative imaging for individual patient management it can be desirable to provide a class of decision support informatics tools to enable further exploiting the capabilities of imaging within the realities of existing tool work flows and/or reimbursement constraints.

Currently, imaging of atherosclerosis is routinely performed both invasively through catheterization as well as non-invasively by ultrasound, CT, MR, and using nuclear medicine techniques. The most typical assessment is luminal stenosis. Recent progress that has been made has been in the determination of fractional flow reserve.

One difficulty with current imaging of atherosclerosis can include lack of robustness in the method used. For example, current methods typically only provide a low level of contrast between blood vessel outer wall and perivascular tissues, thus making it difficult to distinguish between the two. Some current methods simply employ annular rings around a lumen without specific determination of outer wall boundary. Vessel tapering, branching vessels, nearby tissues, etc. can also be problematic.

Another difficulty with current imaging of atherosclerosis can be due to a particular imaging device interrogating tissue using a limited excitation, and that despite the utility of multi-contrast MR on the one hand, or multi-energy CT on the other, the result can be a degree of non-specific response in the produced signal.

SUMMARY OF THE INVENTION

Currently difficulties with the recent progress can include difficulty with interpreting raw pixel reconstructed intensity values using simplistic thresholding operators. One aspect of this is that the physical imaging modality intrinsically limits the degree to which the pixel values are correct manifestations of the object being imaged, for example due to the fact that a given point is actually spread or blurred according to the finite physical characteristics of the imaging. For example, at the submillimeter scale of this analysis, scanner blur (e.g., manifestations such as "calcium blooming") plays a dominant role in quantitative accuracy and, thus, we compensated for the imaging system point spread function. Additionally, heterogeneity of tissues both within and outside the vessel wall present classification and measurement challenges unless processed effectively.

In one aspect, the invention includes a system comprising a processor and a non-transient storage medium including processor executable instructions implementing an analyzer module including a hierarchical analytics framework. The hierarchal analytics framework can be configured to utilize a first set of machine learned algorithms to identify and quantify a set of biological properties utilizing medical imaging data segment the medical imaging data based on the quantified biological properties to delineate existence of perivascular adipose tissue.

In some embodiments, segmenting the medical imaging data further comprises segmenting the medical imaging data into at least a lumen boundary and an outer wall boundary. In some embodiments, the analyzer module is configured to partition a lumen and an outer wall based on the segmented lumen boundary and outer wall boundary into one or more vessel boundaries.

In some embodiments, the biological properties include calcified regions, LRNC regions, intra-plaque regions, matrix regions, or any combination thereof. In some embodiments, delineating the perivascular adipose tissue further includes creating an evaluation region by extending the outer wall boundary by a predetermined distance and utilizing a second set of machine learned algorithms to identify whether the evaluation region includes the perivascular adipose tissue.

In some embodiments, the analyzer module is configured to determine maximum, minimum, mean or any combination thereof a cross-sectional area of the perivascular adipose tissue. In some embodiments, the analyzer module is configured to, for each partition, determine a maximum, minimum, mean or any combination thereof of a cross-sectional area of each of the one more vessels boundaries.

In some embodiments, the analyzer module is configured to, for each partition, determine volume of each of the one more vessels boundaries. In some embodiments, the analyzer module is configured to determine maximum, minimum, mean or any combination thereof of a cross-sectional area for a target.

In some embodiments, segmenting the medical image data further comprises segmenting the medical image data into three-dimensional (3D) objects.

In another aspect, the invention involves a system including a processor and a non-transient storage medium including processor executable instructions implementing an analyzer module including a hierarchical analytics framework. The hierarchical analytics framework can be configured to utilize a first set of machine learned algorithms to identify and quantify a set of biological properties utilizing medical imaging data, wherein the biological properties include LRNC regions of a blood vessel and segment the medical imaging data based on the quantified biological properties to determine a lumen boundary and determine a cap thickness based on a minimum distance between the lumen boundary and LRNC regions.

In some embodiments, segmenting the medical imaging data further comprises segmenting the medical imaging data into an outer wall boundary. In some embodiments, the analyzer module is configured to partition a lumen and an outer wall based on the segmented lumen boundary and outer wall boundary into one or more vessel boundaries. In some embodiments, the biological properties include calcified regions, LRNC regions, intra-plaque regions, matrix regions, or any combination thereof.

BRIEF DESCRIPTION OF THE DRAWINGS

Non-limiting examples of embodiments of the disclosure are described below with reference to figures attached hereto that are listed following this paragraph. Dimensions of features shown in the figures are chosen for convenience and clarity of presentation and are not necessarily shown to scale.

The subject matter regarded as the invention is particularly pointed out and distinctly claimed in the concluding portion of the specification. The invention, however, both as to organization and method of operation, together with objects, features and advantages thereof, can be understood by reference to the following detailed description when read with the accompanied drawings. Embodiments of the invention are illustrated by way of example and not limitation in the figures of the accompanying drawings, in which like reference numerals indicate corresponding, analogous or similar elements, and in which:

It will be appreciated that for simplicity and clarity of illustration, elements shown in the figures have not necessarily been drawn accurately or to scale. For example, the dimensions of some of the elements can be exaggerated relative to other elements for clarity, or several physical components can be included in one functional block or element.

DETAILED DESCRIPTION

Figure 1:
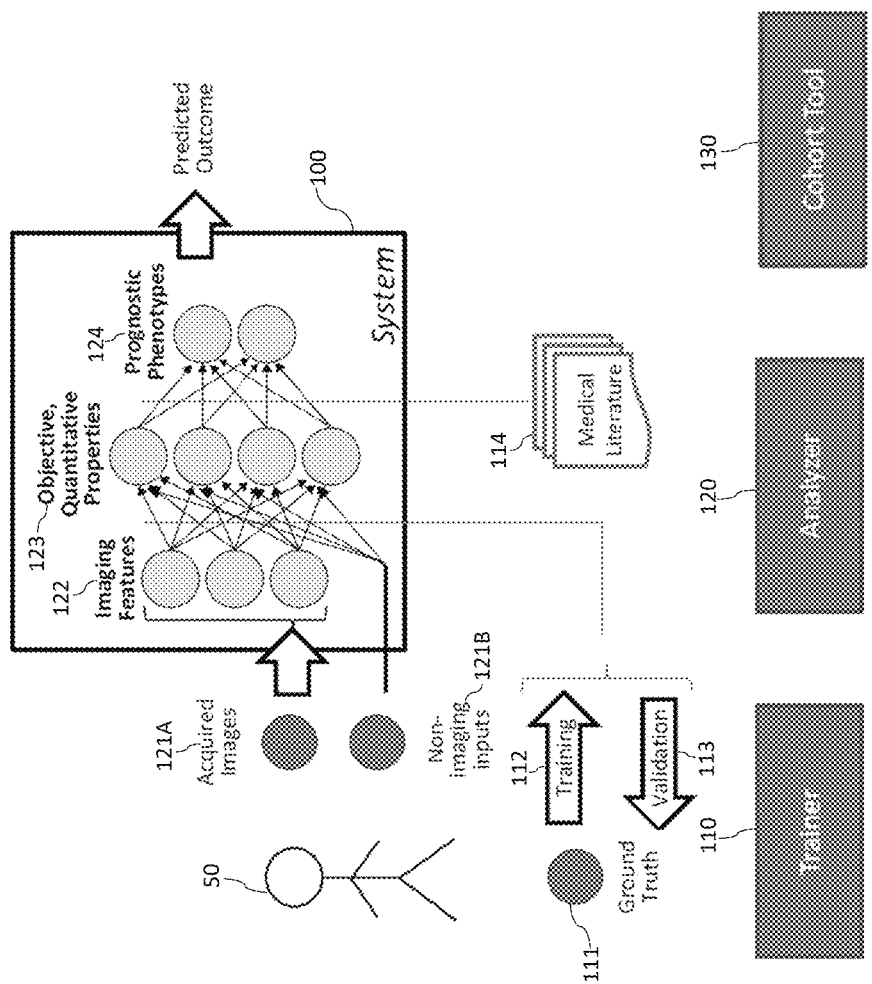
FIG. 1 is a diagram of a system for determining and characterizing a medical condition by implementing a hierarchical analytics framework, according to some embodiments of the invention.

FIG. 1 is a diagram of a system for determining and characterizing a medical condition by implementing a hierarchical analytics framework, according to some embodiments of the invention. The system 100 can include a trainer module 110, an analyzer module 120 and a cohort tool module 120.

The analyzer module 120 can include a hierarchical analytics framework which can identify and/or quantify biological properties/analytes 130 based on medical imaging data (e.g., medical imaging data of patient). The medical imaging data can include (i) imaging features 122 from one or more acquired images 121A of a patient 50 and/or (ii) non-imaging input data 121B for a patient 50. The analyzer module 120 can identify and/or characterize one or more pathologies (e.g., prognostic phenotypes) 124 based on the quantified biological properties/analytes 123. The analyzer module 120 can operate independent of ground truth and/or validation references by implementing one or more pre-trained algorithms, e.g., machine learned algorithms, for drawing inferences.

In some embodiments, the analyzer module 120 includes algorithms for calculating imaging features 122 from the acquired images 121A of the patient 50. In various embodiments, the image features 122 are computed on a per-voxel basis, on a region-of-interest basis, or any combination thereof. In some embodiments, non-imaging inputs 121B that can be utilized in calculating imaging features 122 include data from laboratory systems, patient-reported symptoms, patient history, or any combination thereof.

The image features 122 and/or non-imaging inputs 121B can be utilized by the analyzer module 120 to calculate the biological properties/analytes 123. The biological properties/analytes are typically quantitative, objective properties (e.g., objectively verifiable rather than being stated as impression or appearances) that may represent e.g., a presence and degree of a marker (such as a chemical substance) or other measurements such as structure, size, or anatomic characteristics of region of interest. In various embodiments, the quantified biological properties/analytes 123 are displayed and/or exported for direct consumption by a user, e.g., by a clinician, in addition to or independent of further processing by the analyzer module 120.

The cohort tool module 130 can define a cohort of patients for group analyses thereof, e.g., based on a selected set of criteria related to the cohort study in question. An example cohort analysis may be for a group of patients enrolled in a clinical trial, e.g., with the patients further being grouped based on one or more arms of the trial for example a treatment vs. control arm. Another type of cohort analysis may be for a set of subjects for which ground truth or references exist, and this type of cohort may be further decomposed into a training set or "development" set and a test or "holdout" set. Development sets may be supported so as to train 112 the algorithms and models within analyzer module 120, and holdout sets may be supported so as to evaluate/validate 113 the performance of the algorithms or models within analyzer module 120.

The trainer module 110 can be utilized to train 112 the algorithms and models within analyzer module 120. The trainer module 110 can rely on ground truth 111 and/or reference annotations 114 so as to derive weights and/or models, e.g., according to established machine learning paradigms or by informing algorithm developers. In some embodiments, the trainer module 110 employs classification and/or regression models. The classification and/or regression modules can be highly adaptable, e.g., capable of uncovering complex relationships among the predictors and the response. However, their ability to adapt to the underlying structure within the existing data can enable the models to find patterns that are not reproducible for another sample of subjects. Adapting to irreproducible structures within the existing data is commonly known as model over-fitting. To avoid building an over-fit model, a systematic approach may be applied that prevents a model from finding spurious structure and enable the end-user to have confidence that the final model will predict new samples with a similar degree of accuracy on the set of data for which the model was evaluated.

Successive training sets may be utilized to determine optimal tuning parameter(s), and a test set may be utilized to estimate an algorithm's or model's predictive performance. Training sets may be used for training each of the classifiers via randomized cross-validation. Datasets may be repeatedly split into training and testing sets and may be used to determine classification performance and model parameters. The splitting of the datasets into training and test sets can occur using a stratified and/or maximum dissimilarity approach. In some embodiments, a re-sampling approach (e.g. bootstrapping) is utilized within the training set in order to obtain confidence intervals for (i) the optimal parameter estimate values, and/or (ii) the predictive performance of the models.

In some embodiments, the classification models may be trained in whole or in part by application of multi-scale modeling techniques, such as for example partial differential equations, e.g., to represent likely cell signaling pathways or plausible biologically-motivated presentations.

In some embodiments, the classification models may be trained as described in U.S. patent Ser. No. 16/203,418, filed on Nov. 28, 2018, incorporated herein by reference in its entirety. In some embodiments, a patient report is generated, for example, as shown FIG. 3 of U.S. patent application Ser. No. 16/203,418, along with the corresponding description. In various embodiments, vessel coordinates and/or topologies are determined, as shown in FIGS. 7, 9, 23, 26, of U.S. patent application Ser. No. 16/203,418, along with the corresponding description. In various embodiments, various analysis, models, and/or analytes are determined, as shown in FIGS. 10, 12, 18, 31, 34 and 39 of U.S. patent Ser. No. 16/203,418, along with the corresponding description. In various embodiments, system architectures are as shown in FIGS. 32, 33 of U.S. patent Ser. No. 16/203,418, along with the corresponding description.

Figure 2:
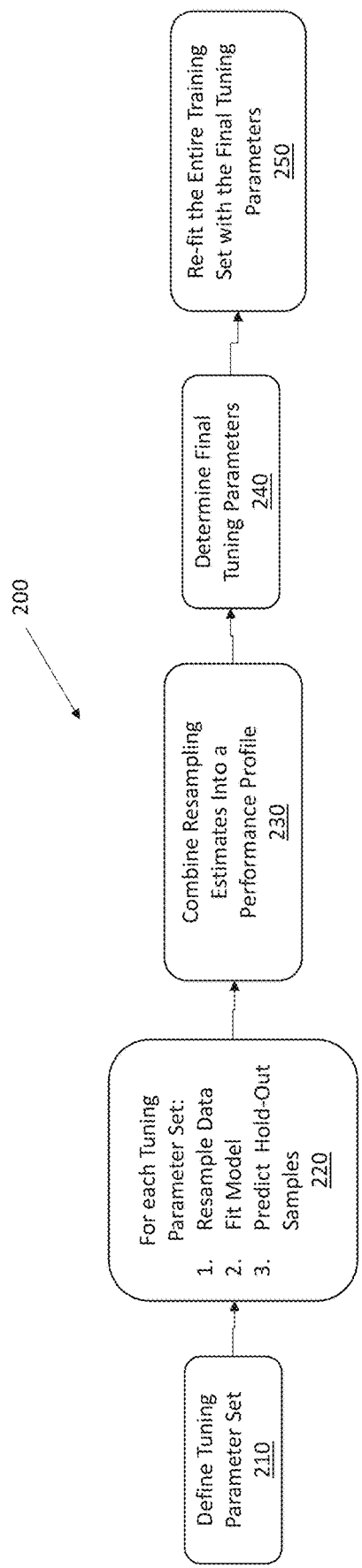
FIG. 2 is a flow chart for a re-sampling based model building method, according to some embodiments of the invention.

FIG. 2 is a flow chart for a re-sampling based model building method 200 which may be utilized by a system (e.g., system 100 as described above with respect to FIG. 1), according to some embodiments of the invention. At step 210, a tuning parameter set can be defined. At step 220, for each tuning parameter set, data (e.g., medical data as described above in FIG. 1) is resampled, a model is fitted and hold-out samples can be predicted. At step 230, resampling estimates can be combined into a performance profile. At step 240, final tuning parameters can be determined. At step 250, the entire training set can be re-fitted with the final tuning parameters. After each model has been tuned from the training set, each model can be evaluated for predictive performance on the test set. Test set evaluation can occur once for each model to, for example, ensure that the model building process does not over-fit the test set. For each model that is constructed, the optimal tuning parameter estimates, the re-sampled training set performance and/or the test set performance can be reported (e.g., transmitted to a display and/or written to a file to include in a report). Actual values of the model parameters over randomized splits can be compared to evaluate model stability and/or robustness to training data.

In some embodiments, one or more models are tuned for each of the biological properties/analytes (e.g., tissue types) represented in ground truth maps (e.g., ground truth 11 as described above). Model responses (e.g., responses from the models as described above) may include, for example, covariance based techniques, non-covariance based techniques, and tree based models. Depending on their construction, endpoints may have continuous and categorical responses; some of the techniques in the above categories are used for both categorical and continuous responses, while others are specific to either categorical or continuous responses. Optimal tuning parameter estimates, the re-sampled training set performance, as well as the test set performance may be reported for each model.

As model complexity grows (e.g., amount of computation, hidden layers, stages of optimization and/or dimensionality of hyperplanes), predictive performance can improve. The performance improvement can be achieved at the expense of model interpretability. For example, the parameter coefficients from a multiple linear regression model intuitively link each predictor to the response. The same kind of interpretation typically cannot be uncovered in a neural network, support vector machine, or many other models as are known in the art. However, these models may provide much better predictive ability, especially if the underlying relationship between the predictors and the response is non-linear. In some embodiments, to extract at least a portion of interpretive information, variable importance calculations are performed. Variable importance projection methods can provide a weight to the individual features based on an extent that the respective individual feature contributes to a low dimensional data representation. For example, for problems where the number of features is equal to or larger than the number of training instances, classifier models can be subject to the "curse of dimensionality" problem.

In some embodiments, the analyzer module 120 provides functionalities as described below in Table 1:

TABLE 1

| | |
|---|---|
| Delineate Field | Register multiple data streams across a field |
| | Segment organs, vessels, lesions, and other application-specific objects |
| | Reformat anatomy for specific analyses |
| Delineate Target | Register multiple data streams at a locale |
| | Fine-grained segmentation |
| | Measure size and/or other relevant anatomic structure |
| | Extract whole-target features |
| Delineate Sub-target regions | Split target into sub-targets according to application |
| | Sub-target specific calculations |
| Delineate Components | (Re—) Segment Component |
| | Calculate Readings |
| | Visualize Probability Map |
| Determine Disease Severity | Determine Phenotype |
| | Predict Outcome |
| Compare Multiple Timepoints | (Optional) Compare Multiple Timepoints |
| Assess multi-focal disease | Aggregate across target lesions over a wide scan field. |
| Generate Patient Report | Generate Patient Report |

As shown in Table 1, the analyzer module 120 can delineate fields, for example, to register multiple data streams across a field; to segment organs, vessels, lesions and other application-specific objects; and/or to reformat/reconfigure anatomy for specific analyses.

In some embodiments, the segmenting the vessels includes segmenting the medical imaging data to one or more parts of a blood vessel, including, a lumen boundary, an outer wall boundary, and/or one or more vessel boundaries based on the identified and quantified biological properties. The biological properties can include calcified regions, LRNC regions, intra-plaque regions, matrix regions, or any combination thereof.

Figure 4:
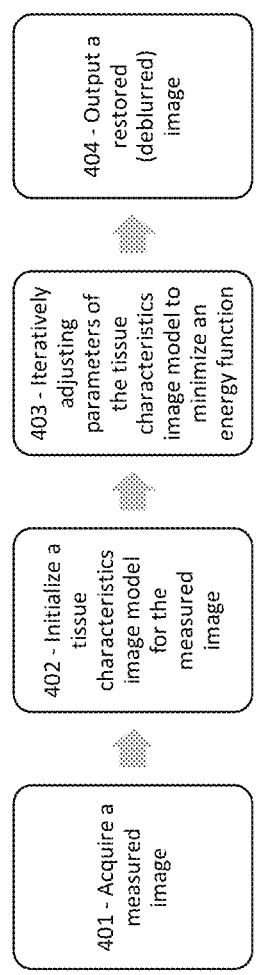
FIG. 4 is a flow chart for a method for restoring and segmenting, according to some embodiments of the invention.

FIG. 4 of U.S. patent Ser. No. 16/203,418, along with the corresponding description, shows an example segmentation levels for a multi-scale vessel wall analyte map, according to the present disclosure.

The analyzer module 120 can delineating a target, for example, a lesion, in a delineated field. Delineating a target may, for example, include registering multiple data streams at a locale; conducting fine-grained segmentation; measuring size and/or other characteristics of relevant anatomic structures; and/or extracting whole-target features (e.g., biological properties/analytes characteristic of the entire target region).

In some embodiments, one or more sub-target regions are delineated. For example, a target region may be split into sub-target regions according to a particular application with sub-target specific calculations (e.g., biological properties/analytes characteristic of a sub-target region). The analyzer module 120 can delineate components and/or relevant features (such as composition), for example, in a particular field, target or sub-target region.

This can include segmenting or re-segmenting the components/features, calculating values for the segmented components/features (e.g., biological properties/analytes characteristic of the component/feature) and assigning a probability map to the readings. Pathologies may be determined, based on the biological quantified properties/analytes, and characterized, e.g., by determining phenotype and/or predictive outcomes for the pathologies.

In some embodiments, the analyzer module 120 compares data across multiple timepoints, e.g., one or more of the biological components/analytes may involve a time based quantification. In further embodiments, a wide scan field may be utilized to asses multi-focal pathologies, e.g., based on aggregate quantifications of biological properties/analytes across a plurality of targets in the delineated field. Finally, based on the forgoing analytics, the analyzer module 120 may be configured to generate a patient report.

Figure 3:
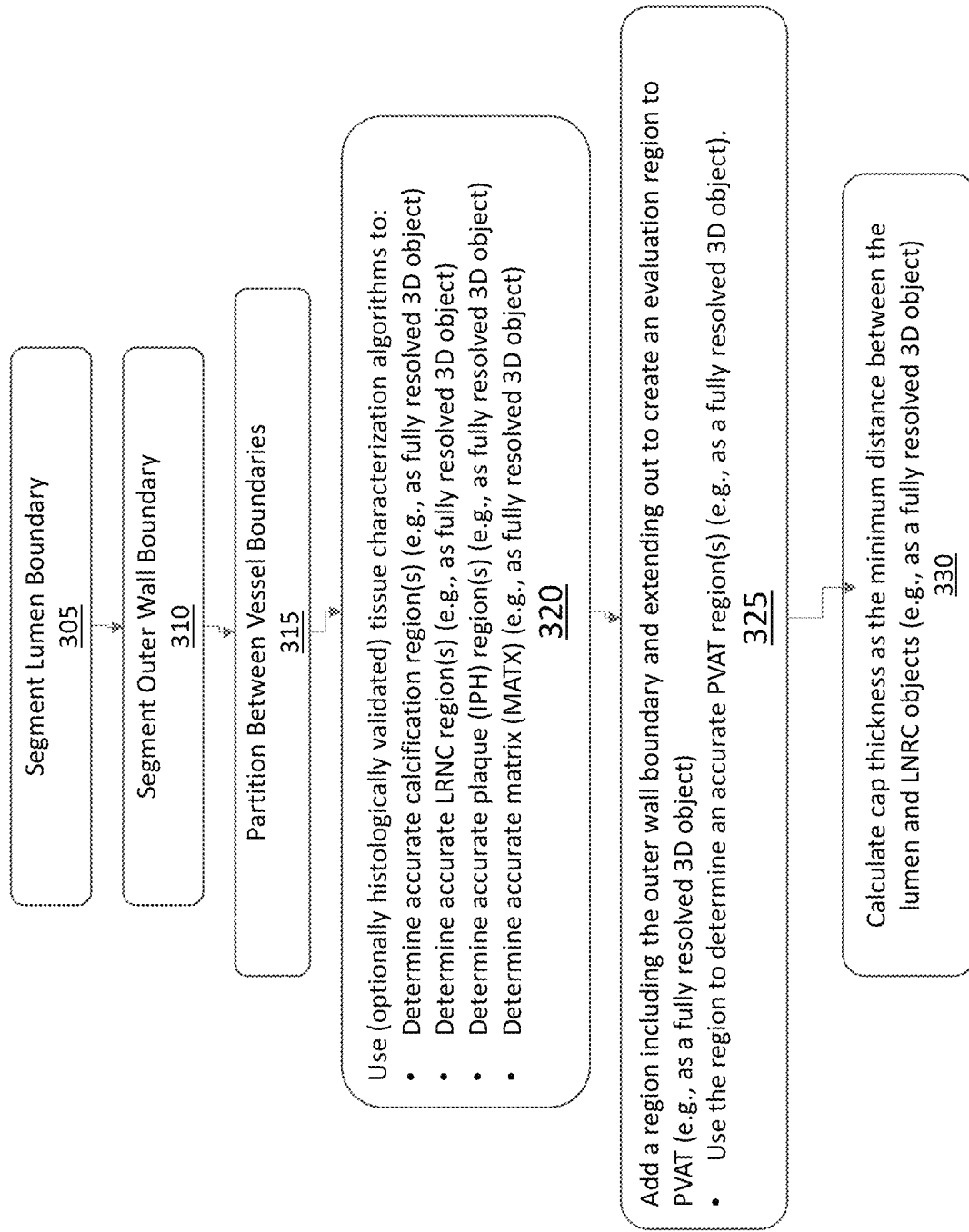
FIG. 3 is a flow chart of a method for delineating existence of perivascular adipose tissue and determining cap thickness based on medical imaging data of a patient, according to some embodiments of the invention.

FIG. 3 is a flow chart of a method for delineating existence of perivascular adipose tissue and determining cap thickness based on medical imaging data of a patient, according to some embodiments of the invention. The medical imaging data can include radiological data and non-radiological data. For example, the medical imaging data can include MRI image information, patient demographic information and/or MRI device information.

The method can involve segmenting a lumen boundary based on the medical imaging data (Step 305). The method can also involve segmenting an outer wall boundary based on the medical imaging data (Step 310). Segmenting the medical image data can involve receiving the medical image data (e.g., from a file, from a user, from another computer and/or from the cloud). The medical imaging data can include data obtained via an MRI, CT, and/or ultrasound device. The medical imaging data can be analyzed (e.g., via analyzing module 120 as described above in FIG. 1), to identify and/or quantify one or more biological properties. In some embodiments, the medical image data can be restored and/or restored/deblurred, as discussed in further detail below.

The medical imaging data can include input from a user that indicates a region of interest containing a physiological target that is to be phenotyped.

Identifying and/or quantifying the one or more biological properties can involve utilizing one or more machine learned algorithms. The machine learned algorithms can be retrieved from a file, input by a user, retrieved from the cloud, or any combination thereof. The machine learned algorithms can be algorithms trained using AlexNet, which is a convolutional neural network (CNN). In some embodiments, the machine learned algorithms are further based on non-image medial data. For example, genomics, proteomics, and/or transcriptomics data.

The one or more biological properties and the medical imaging data itself can be used for segmenting into two-dimensional (2D) or three-dimensional (3D) objects. For example, upon segmenting the lumen boundary, a lumen of the blood vessel can be visualized in 3D. Similarly, upon segmenting the outer wall boundary, the outer wall can be visualized in 3D.

In some embodiments, prior to segmenting a user viewing a volume rendering of the blood vessel defines an initial vessel centerline. The segmenting of the lumen can be performed by a thresholding level set evolution using the optimal local Otsu threshold. The segmenting of the outer wall can be performed by using a geodesic active contour level set evolution, initialized with the lumen segmentation and initial centerline. In some embodiments, the lumen and/or outer wall can be manually edited by a user, for example, via a user input device.

In some embodiments, centerline paths are determined by defining a speed function for a fast marching algorithm. In the lumen interior, the speed function can be a linear function of distance from the lumen boundary and outside of the lumen. A small nonzero value can be used to, for example, allow for pathfinding across complete stenoses. Gradient descent can be used to define an initial centerline, which can be further centralized by a ball-and-spring model that optimizes monotonic equal spacing and distance from the lumen boundary.

The method can involve partitioning (e.g., bifurcating) vessel boundaries (Step 315). Partitioning vessel boundaries can be based on the segmented lumen boundary and outer wall boundary into one or more vessel boundaries. The one or more vessel boundaries can be partitioned into 2D or 3D objects.

In some embodiments, partitioning the vessel boundaries involves applying image registrations utilizing Mattes mutual information (MR), mean square error (CT) metric, rigid versor transform and/or LBFGSB optimizer, as examples. An initial lumen segmentation can utilize a confidence connected filter (e.g., coronary, carotid, vertebral and/or femoral) to distinguish the lumen. Lumen segmentation can utilize MR imaging (such as a combination of normalized, e.g., inverted for dark contrast, images) or CT imaging (such as use of registered pre-contrast, post-contrast CT and 2D Gaussian distributions) to define a vessel-ness function. Various components that are nearby but not necessarily connected can be dilated to connect them, e.g., by analyzing and applying thresholding may be applied.

In some embodiments, partitioning the vessels involves outer wall segmentation (e.g., utilizing a minimum curvature (k2) flow to account for lumen irregularities). In some embodiments, an edge potential map is calculated as outward-downward gradients in both contrast and non-contrast. In some embodiments, outer wall segmentation utilizes cumulative distribution functions (incorporating prior distributions of wall thickness, e.g., from 1-2 adjoining levels) in a speed function to allow for median thickness in the absence of any other edge information. In some embodiments, ferret diameters are employed for vessel characterization. In some embodiments, wall thickness is calculated as the sum of the distance to lumen plus the distance to the outer wall. In some embodiments, lumen and/or wall segmentations are performed using semantic segmentation using, for example, CNNs. The lumen and wall segmentations can be partitioned according to path segments by using a greedy fast marching competition from all the path points of the three segments, resulting in three mutually exclusive partitions of each segmentation.

The method can involve determining one or more of calcified regions, LRNC regions, intra-plaque hemorrhage regions, matrix regions based on the segmentations (e.g., as the segmentations are based on quantified biological properties) (Step 320).

The method can involve delineating the perivascular adipose tissue, wherein delineating the perivascular adipose tissue can involve creating an evaluation region by extending the outer wall boundary by a predetermined distance and utilizing a second set of machine learned algorithms to identify whether the evaluation region includes the perivascular adipose tissue (Step 325). The predetermine distance can be input by a user, retrieved from a file, or based on quantified biological properties.

In some embodiments, the outer wall boundary is extended as a 3D object. In these embodiments, the outer wall boundary is extended by a predetermined volume. The predetermined volume can be input by a user, retrieved from a file or based on quantified biological properties.

In some embodiments, identifying whether the evaluation region include the perivascular adipose tissue involves employing one or more algorithms for evaluating vascular and perivascular structure. The system (e.g., system 100 as described above in FIG. 1) can employ a target/vessel segment/cross-section model for segmenting the underlying structure of an imaged vessel. In some embodiments, luminal irregularities and/or plaque structure (e.g., remodeling) are evaluated. In some embodiments, a maximum, minimum, mean or any combination thereof of a cross-sectional area of the perivascular adipose tissue is determined.

In some embodiments, a maximum, minimum, mean or any combination thereof of a cross-sectional area of each of the one more vessel boundaries is determined. In some embodiments, a volume of each of the one more vessel boundaries is determined.

In some embodiments, evaluating the vascular and perivascular composition (within the wall, e.g., cross-sectional area and volume of lipid-rich necrotic core (LRNC) and how close to the lumen it is (e.g., cap thickness)), and/or perivascular tissue characteristics, e.g., perivascular adipose tissue (PVAT) can involve the model accounting for an observed image intensity at a pixel or voxel being influenced by a local neighborhood of hidden analyte category nodes thereby accounting for partial volume and scanner point spread function (PSF).

For example, FIG. 4 of U.S. patent application Ser. No. 16/203,418, depicts a multi-scale vessel wall analyte map that includes a wall-level segmentation 410 (e.g., a cross-sectional slice of the vessel), blob-level segmentation and pixel-level segmentation 430 (e.g., based on individual image pixels.

The method can also involve determining cap thickness (e.g., a layer of tissue that can be described as a cap) based on a minimum distance between the lumen boundary and LRNC regions (Step 330). The minimum distance between the lumen boundary and LRNC regions can be determined by creating first vector between a voxel in the lumen and voxel in the LNRC, determining the distance of the vector, creating a second vector between a different voxel point in the lumen and a different voxel in the LNRC, determining the distance and comparing against the first determined distance, and keeping the shortest of the two. Performing these steps for additional lumen and LNRC voxels to find the shortest voxel and assigning that as the cap thickness.

In some embodiments, parameters related to cross-section of tissues are determined and/or output. For example, cross section within each positioned and oriented slab, maximum, mean, minimum, and/or area of tissue characteristics in-wall (e.g., within the outer wall boundary) and/or perivascular.

In some embodiments, parameters related to one or more vessels are determined and/or output. For example, within each partition as described above, a maximum, mean, and/or minimum cross-section measurements across all the cross-sections included in each respective vessel can be determined and/or output. Within each partition, a volume and/or volume proportion can be determined and/or output (e.g., for 3D objects). In some embodiments, parameters related to a target (e.g., a group of vessels). In some embodiments, determining the parameters related to a target involves perform similar functions as the vessel level, but for the target as a whole.

In some embodiments, the readings can be marshalled for ML (e.g., out to training sets and/or in for per-patient inference). In some embodiments, the readings can be marshalled for ML either alone or with non-imaging data, e.g., bloodwork and/or transcriptomics in curated tissue collections.

In some embodiments, for each cross-section, images are stored (e.g., optionally enhanced) for DL (e.g., out to training sets and/or in for per-patient inference) In some embodiments, the images are stored for DL either alone or with non-imaging data, e.g., bloodwork and/or transcriptomics in curated tissue collections.

Figure 3A:
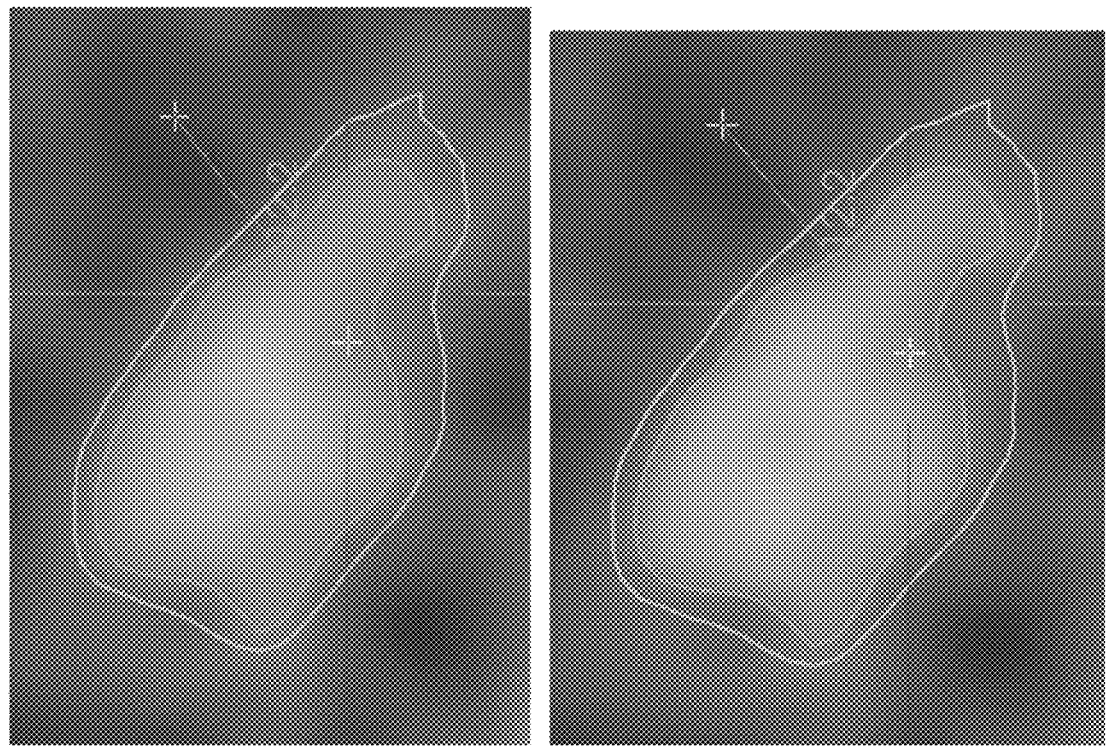
FIG. 3A is a diagram showing effects of restoring as can affect accurate quantitation of tissues, being a cross section through a coronary artery with intensity profiles for the original source CT and after the model-based restoring, according to some embodiments of the invention.
Figure 3A:
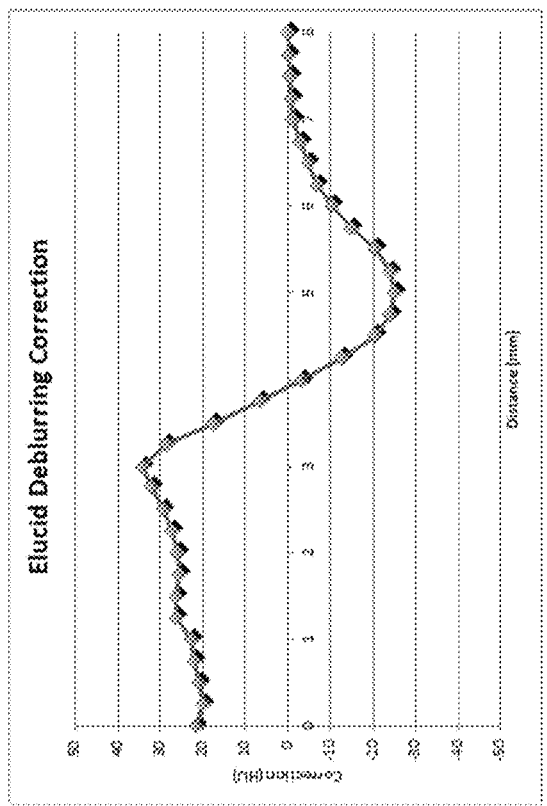

FIG. 3A, The restored/deblurred image shows a cross section through a coronary artery with intensity profiles for an original source CT scan after restoring according to methods described above (e.g., FIGS. 4 and 5) are applied. The change in comparison to the original image can be on the order of +/−30 HU.

In some scenarios, more subtle tissue characteristics are too prone to blurring artifacts for initial estimation from the source CT images, as exemplified in FIG. 3A. FIG. 3A is a diagram showing effects of restoring as can affect accurate quantitation of tissues, being a cross section through a coronary artery with intensity profiles for the original source CT and after the model-based restoring. For PVAT, one assumption can be that its fully adipose tissue is −00 HU while water due to inflammation is 0 HU such that adipose tissue with some inflammation would be somewhere in between −100 and 0 HU depending on how much water has entered the tissue. If, for example, tissue were 50% adipose tissue and 50% water from inflammation, a change of 50 HU can be achieved, which may be negated by uncorrected for CT blur, thus making a potentially good biomarker ineffective.

As described above, in some embodiments, the medical image data can be restored and/or restored/deblurred. For example, FIG. 21 of U.S. patent application Ser. No. 16/203,418 shows an example of a pre-processing step of restoring using a patient-specific point spread determination algorithm to mitigate artifacts and/or image limitations that can result from the image formation process that can, for example, decrease the ability to determine characteristics predictive of the phenotype. The figure can demonstrates a portion of the radiology analysis application analysis of a plaque from a CT. As shown in the figure, the restored/deblurred or restored images that are a result of iteratively fitting a physical model of the scanner point spread function with regularizing assumptions about the true latent density of different regions of the image.

In some embodiments, restoring of the image can be performed as follows: An imaging device (such as an MRI or CT device) can be used to acquire a measured image. A tissue characteristics image model can be initialized for the measured image representing a true underlying image. A tissue characteristics model can apply a level-set method (LSM) as a conceptual framework for numerical analysis of surfaces and shapes in the image representing biological analytes. The tissue characteristics model can map level sets to the image data via a set of characteristic equations, and thereby can represent specific biological analytes. The characteristic equations can be utilized to solve an optimization problem to determine optimal transformation parameters for the tissue characteristics model, and can thereby optimize restoring for segmentation of the specific biological analytes being analyzed. The tissue characteristics model and/or the optimization parameters can advantageously account/make use of a knowledge base of the underlying biology of the system, e.g., based on biological models for the analytes. The optimization problem can be solved using an iterative process which iteratively adjusts the tissue characteristics image model in order to minimize an energy function which models imaging physics relating to the appearance of different analytes in a Bayesian framework (e.g., energy may be the negative log of probabilities for the Bayesian framework integrated over the image). A restored/deblurred image may be outputted based on the transform parameters determined from the optimization problem. The restored/deblurred image can include restoring which can be optimized for segmentation and/or for quantitative analysis of the biological analytes. This can represent a significant improvement over generalized restoring techniques that have not accounted for the underlying biology of the system being analyzed.

Various advantages and improvements can be provided by restoring, for example, removing of blur that derives from very bright as well as very dark signals. Unlike conventional techniques, this may advantageously, account for both the technical image formation process in the scanner, as well as the specific biology being imaged. Additional advantages can include deriving scanner blur based on the image and incorporating detailed statistical models of prior estimates of tissue characteristics drawn from a truth source, e.g., such as histopathology.

In some embodiments, prior estimates used inform the classification process so as to provide the most plausible explanation for the observed image data. Additional advantages can include increased accuracy in readings of biological analytes, e.g., that include cross-sectional areas, volumes, and spatial locations for different types of tissues.

FIG. 4 is a flow chart for a method for restoring and segmenting, according to some embodiments of the invention. The method can involve acquiring a measured image (Step 401) via an imaging device. The method can also involve initializing a tissue characteristics image model for the measured image that represents a true underlying image (Step 402). In some embodiments, initializing a tissue characteristics image model can involve Initializing $\phi i$ level set functions and $\chi i$ characteristic functions and Initializing g with the background region masked to a constant intensity.

The method can also involve solving an optimization algorithm using an iterative process which can iteratively adjust the tissue characteristics image model in order to minimize an energy function which models imaging physics relating to the appearance of different analytes (Step 403). In some embodiments, the optimization algorithm involves:

Until stopping_criterion
  a. Compute characteristic functions $\chi I$,
  b. Compute blurred characteristic functions $h*\chi I$,
  c. Compute constants $c_i$,
  d. Compute $d\phi i/dt$ level set function updates,
    i. Create image f with partial volume effect at edges
    ii. Create image $h*f$;

Volume fractions are computed from characteristic functions.

In some embodiments, a stopping criterion for the iterations can be based upon one or more user-defined number of iterations.

The optimization algorithm can use the iterative process as shown below in FIG. 5.

The method can also involve outputting a restored/deblurred image based on the transform parameters determined from the optimization algorithm (Step 404). In some embodiments, outputting a restored/deblurred image involves outputting restored/deblurred image is provided as Irestored/deblurred=g−(h*f−f).

Figure 5:
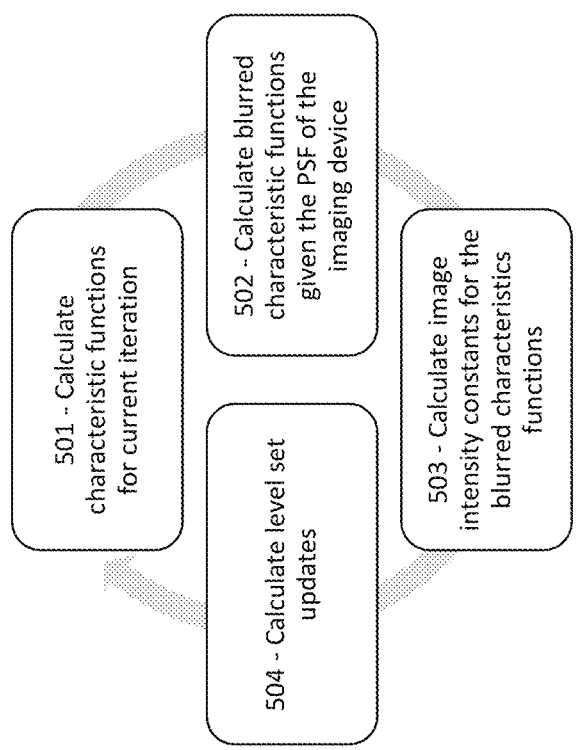
FIG. 5 is a flow chart for a method of an iterative optimization algorithm, according to some embodiments of the invention.

FIG. 5 is a flow chart for a method of an iterative optimization algorithm step (e.g. step 403 of FIG. 4) as applied within the context of multi multi-phase level sets where analyte image regions are defined by characteristic functions as a function of level set functions for each tissue characteristic type. The method can involve calculating characteristic functions from the level set functions for the current iteration, for example, based on the current level sets (Step 501). The method can also involve calculating blurred character characteristic functions calculated from the characteristic functions, e.g., based on a IIR Gaussian blurring given a point spread function (PSF) for the imaging device (Step 502). The method can also involve, calculating image intensity constants for the blurred characteristic functions (Step 503). The method can also involve calculating level set updates, e.g., based on a gradient decent approach to minimizing an energy function (Step 504). The iterative process reinitializes the level sets and characteristic equations with every iteration (e.g., prior to repeating steps 501-504). Thus, a signed distance property of the level set functions is relaxed during each iteration until reinitialization after the iteration.

Figure 6:
FIG. 6 is an example of an acquired image which includes blurring, according to the prior art.
Figure 7B:
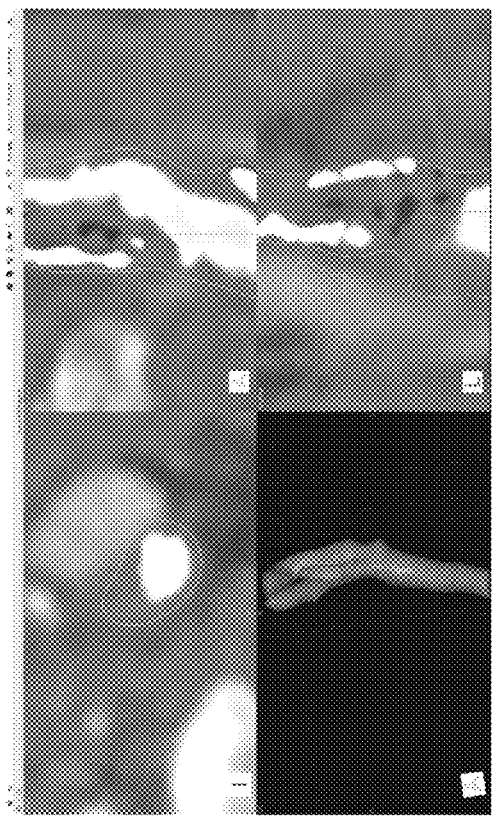
FIGS. 7A and 7B shows examples of an acquired image which before and after restoring, respectively, according to some embodiments of the invention.
Figure 7A:
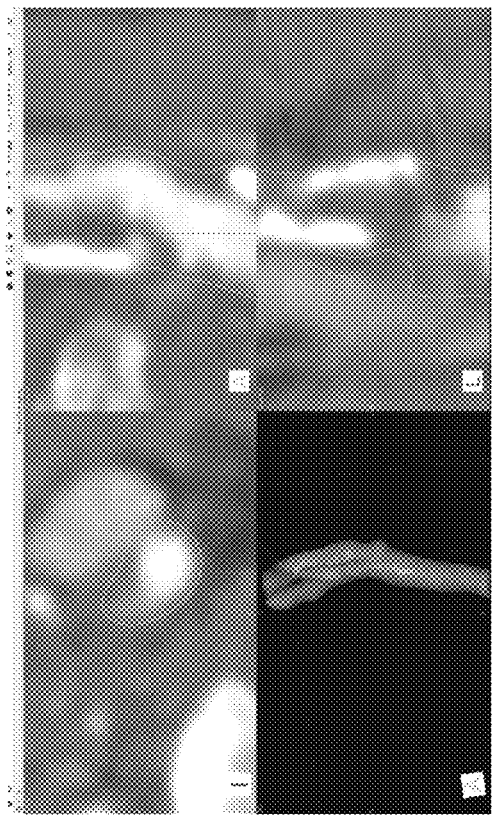
Figure 8B:
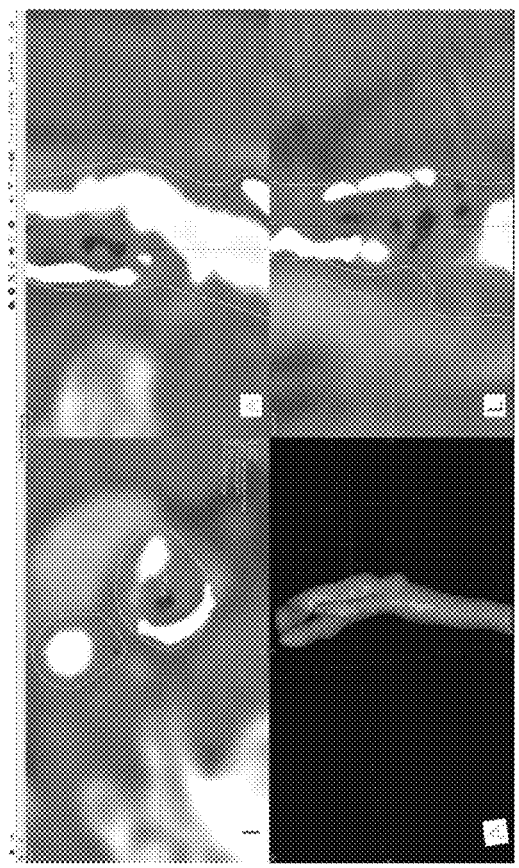
FIGS. 8A and 8B shows examples of an acquired image which before and after restoring, respectively, according to some embodiments of the invention.
Figure 8A:
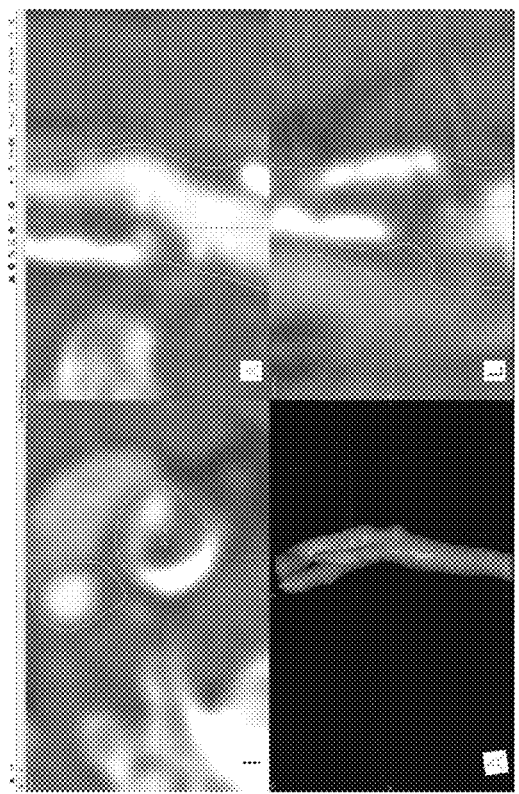

FIGS. 6, 7A-7B and 8A-8B can illustrate effectiveness of the restoring/segmentation as described above. In particular, FIG. 6 is an example of an acquired image which includes blurring. FIG. 7A shows an example of an acquired image which includes blurring and FIG. 7B shows the same acquired image of FIG. 7A after restoring and segmenting according to embodiments of the invention applied herein are applied. FIG. 8A shows another example of another acquired image which includes blurring and FIG. 8B shows the same acquired image of FIG. 7A after restoring and segmenting according to embodiments of the invention applied herein are applied. As shown in FIGS. 7A-7B and 8A-8B, the restoring and/or segmentation method of the invention can advantageously provide for improved recognition of biological analytes. In some embodiments, a restored/deblurred image is augmented by replacing segmented regions representing biological analytes with an overlay map (e.g., a color-coded overlay map) for the segmented regions.

Figure 9:
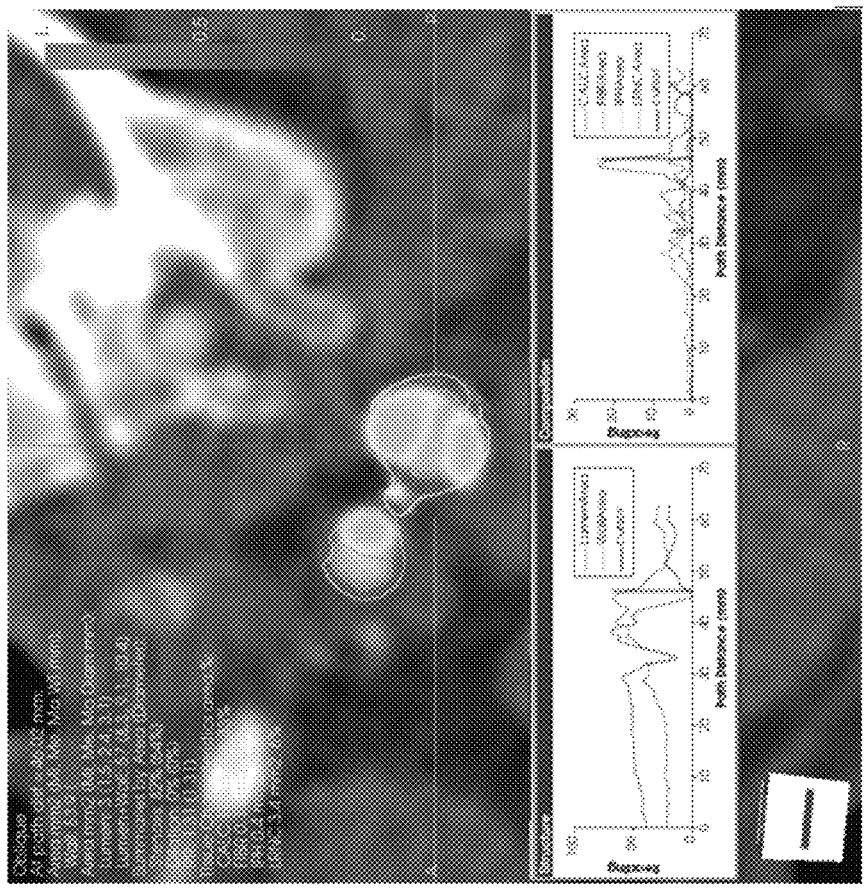
FIG. 9 shows an example of an augmented restored/deblurred image, according to some embodiments of the invention.

FIG. 9 shows an example of an augmented restored/deblurred image, according to some embodiments of the invention.

The augmented restored/deblurred image can depict quantitative measurements associated with identified analyte regions as well as one or more graphical characterizations of structure and/or composition. Thus, the augmented restored/deblurred image may advantageously provide improved tools for a clinician to evaluate a pathology of the patient.

Because the geometry of the wall may be significantly non-circular, the radial distance may be defined based on the shortest distance to the inner luminal surface and the shortest distance to the outer adventitial surface. The expert-annotation of the histology images includes regions that define the lumen and the vessel (defined as the union of the lumen and vessel wall).

A signed distance function can be created for each of these, $L(x)$ and $V(x)$, respectively. The convention is that the interior of these regions is negative so that in the wall L is positive and V is negative. The relative radial distance is computed as $r(x)=L(x)/(L(x)-V(x))$. It has a value of 0 at the luminal surface and 1 at the adventitial surface. The direction of the r-axis is determined by $\nabla r(x)$.

In some embodiments, one level set may be used for the entire vessel lumen initialized with the segmented lumen L. Each distinct contiguous bright region can be initialized as its own level set and calculated as follows: Candidate bright regions are computed using a morphological watershed applied to the inverted image (to turn bright peaks into catchment basins).

In some embodiments, energy functionals can represents an approach that integrates modeling between imaging physics and biology. The imaging physics portion can account for image intensities and the PSF of the scanner while the biological portion of the model incorporates histology-driven knowledge of the structure and growth patterns of atherosclerotic plaques. The model prior weights the model toward the most likely configurations and away from physically and biologically unrealistic solutions. The model can be provided in probabilistic terms and the energy is the negative log of probabilities integrated over the image. In addition to providing analytic tractability, the logarithm super-linearly weights against decreasing probability solutions.

In some embodiments, a Naïve Bayes [10] domain independence assumption is made between imaging physics and biology, e.g., that the likelihood of the residual between blurred model and blurred acquired image does not depend on the biological likelihood of a configuration of tissue characteristic regions next to each other.

The various model parameters that can be evolved throughout the algorithm include the level set functions mapped over the image, the true (e.g., restored/deblurred) image intensity of different biological tissue characteristics, and the width of the scanner PSF. The pre-learned model parameters can include the model of the dependencies of the spatial distribution of tissue characteristics with a plaque.

In some embodiments, after initialization, the model is iteratively adjusted in order to minimize the energy function through a gradient descent trajectory. The gradient descent approach can allows for the direct adjustment of model parameters, such as each level set 0, in order to minimize energy.

An imaging physics term in the energy functional can represent the L2 norm of the difference between the blurred idealized piecewise constant image and the acquired image. The coefficients can allow for a balance between the effect of curvature evolution smoothing and minimizing the mode-to-image residual. The evidence variables can be the acquired image pixel intensities represented by the blurred image g. Within each iteration, the ordering of sub-steps can follow the flow of information through the variables.

The characteristic functions can serve as an intermediary and the Euler-Lagrange equation can be determined in terms of the level set functions. The energy functional can be minimized using a gradient descent approach that moves each $\phi$ toward the local minimum of E at every point in space simultaneously and independently. Within each iteration, the signed distance property of the level set functions can be relaxed until reinitialization after the iteration and thus the integral disappears.

One advantage of the invention can include corrections to the image, (h*f−f), can be low frequency in that they can be simply step edges blurred by a Gaussian thereby preventing erroneous amplification of high frequency noise, which may often occur with conventional deconvolution techniques that may never fully separate amplifying true image structure from amplifying image noise. In fact the error of this improved deconvolution process may be subject only (or substantially only) to the accuracy of the region image intensity constants, the location of the edges, and/or the imaging system blur, all of which can be highly intuitive and can easily be visually confirmed by the end user.

Although embodiments of the invention are not limited in this regard, discussions utilizing terms such as, for example, "processing," "computing," "calculating," "determining," "establishing", "analyzing", "checking", or the like, can refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that can store instructions to perform operations and/or processes.

Although embodiments of the invention are not limited in this regard, the terms "plurality" and "a plurality" as used herein can include, for example, "multiple" or "two or more". The terms "plurality" or "a plurality" can be used throughout the specification to describe two or more components, devices, elements, units, parameters, or the like. The term set when used herein can include one or more items. Unless explicitly stated, the method embodiments described herein are not constrained to a particular order or sequence. Additionally, some of the described method embodiments or elements thereof can occur or be performed simultaneously, at the same point in time, or concurrently.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions of the invention by operating on input data and generating output. Method steps can also be performed by an apparatus and can be implemented as special purpose logic circuitry. The circuitry can, for example, be a FPGA (field programmable gate array) and/or an ASIC (application-specific integrated circuit). Modules, subroutines, and software agents can refer to portions of the computer program, the processor, the special circuitry, software, and/or hardware that implement that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can be operatively coupled to receive data from and/or transfer data to one or more mass storage devices for storing data (e.g., magnetic, magneto-optical disks, or optical disks).

Data transmission and instructions can also occur over a communications network. Information carriers suitable for embodying computer program instructions and data include all forms of non-volatile memory, including by way of example semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

To provide for interaction with a user, the above described techniques can be implemented on a computer having a display device, a transmitting device, and/or a computing device. The display device can be, for example, a cathode ray tube (CRT) and/or a liquid crystal display (LCD) monitor. The interaction with a user can be, for example, a display of information to the user and a keyboard and a pointing device (e.g., a mouse or a trackball) by which the user can provide input to the computer (e.g., interact with a user interface element). Other kinds of devices can be used to provide for interaction with a user. Other devices can be, for example, feedback provided to the user in any form of sensory feedback (e.g., visual feedback, auditory feedback, or tactile feedback). Input from the user can be, for example, received in any form, including acoustic, speech, and/or tactile input.

The computing device can include, for example, a computer, a computer with a browser device, a telephone, an IP phone, a mobile device (e.g., cellular phone, personal digital assistant (PDA) device, laptop computer, electronic mail device), and/or other communication devices. The computing device can be, for example, one or more computer servers. The computer servers can be, for example, part of a server farm. The browser device includes, for example, a computer (e.g., desktop computer, laptop computer, and tablet) with a World Wide Web browser (e.g., Microsoft® Internet Explorer® available from Microsoft Corporation, Chrome available from Google, Mozilla® Firefox available from Mozilla Corporation, Safari available from Apple). The mobile computing device includes, for example, a personal digital assistant (PDA).

Website and/or web pages can be provided, for example, through a network (e.g., Internet) using a web server. The web server can be, for example, a computer with a server module (e.g., Microsoft® Internet Information Services available from Microsoft Corporation, Apache Web Server available from Apache Software Foundation, Apache Tomcat Web Server available from Apache Software Foundation).

The storage module can be, for example, a random access memory (RAM) module, a read only memory (ROM) module, a computer hard drive, a memory card (e.g., universal serial bus (USB) flash drive, a secure digital (SD) flash card), a floppy disk, and/or any other data storage device. Information stored on a storage module can be maintained, for example, in a database (e.g., relational database system, flat database system) and/or any other logical information storage mechanism.

The above-described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of digital data communication (e.g., a communication network). Examples of communication networks include a local area network (LAN), a wide area network (WAN), the Internet, wired networks, and/or wireless networks.

The system can include clients and servers. A client and a server are generally remote from each other and typically interact through a communication network. The relationship of client and server arises by virtue of computer programs running on the respective computers and having a client-server relationship to each other.

The above described networks can be implemented in a packet-based network, a circuit-based network, and/or a combination of a packet-based network and a circuit-based network. Packet-based networks can include, for example, the Internet, a carrier internet protocol (IP) network (e.g., local area network (LAN), wide area network (WAN), campus area network (CAN), metropolitan area network (MAN), home area network (HAN), a private IP network, an IP private branch exchange (IPBX), a wireless network (e.g., radio access network (RAN), 802.11 network, 802.16 network, general packet radio service (GPRS) network, HiperLAN), and/or other packet-based networks. Circuit-based networks can include, for example, the public switched telephone network (PSTN), a private branch exchange (PBX), a wireless network (e.g., RAN, Bluetooth®, code-division multiple access (CDMA) network, time division multiple access (TDMA) network, global system for mobile communications (GSM) network), and/or other circuit-based networks.

Some embodiments of the present invention may be embodied in the form of a system, a method or a computer program product. Similarly, some embodiments may be embodied as hardware, software or a combination of both. Some embodiments may be embodied as a computer program product saved on one or more non-transitory computer readable medium (or media) in the form of computer readable program code embodied thereon. Such non-transitory computer readable medium may include instructions that when executed cause a processor to execute method steps in accordance with embodiments. In some embodiments the instructions stores on the computer readable medium may be in the form of an installed application and in the form of an installation package.

Such instructions may be, for example, loaded by one or more processors and get executed. For example, the computer readable medium may be a non-transitory computer readable storage medium. A non-transitory computer readable storage medium may be, for example, an electronic, optical, magnetic, electromagnetic, infrared, or semiconductor system, apparatus, or device, or any combination thereof.

Computer program code may be written in any suitable programming language. The program code may execute on a single computer system, or on a plurality of computer systems.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

In the foregoing detailed description, numerous specific details are set forth in order to provide an understanding of the invention. However, it will be understood by those skilled in the art that the invention can be practiced without these specific details. In other instances, well-known methods, procedures, and components, modules, units and/or circuits have not been described in detail so as not to obscure the invention. Some features or elements described with respect to one embodiment can be combined with features or elements described with respect to other embodiments.

What is claimed is:

1. A system comprising a processor and a non-transient storage medium including processor executable instructions implementing an analyzer module including a hierarchical analytics framework configured to:
    utilize a first set of machine learned algorithms to identify and quantify a set of biological properties utilizing medical imaging data, wherein the biological properties include LRNC regions of a blood vessel, wherein the medical imaging data is computer tomography (CT) data;
    segment the medical imaging data based on the quantified biological properties to determine a lumen boundary; and
    determine a cap thickness based on a minimum distance between the lumen boundary and LRNC regions, wherein the determining the minimum distance between the lumen boundary and the LRNC regions comprises:
    creating first vector between a first voxel in the lumen and first voxel in the LNRC,
    determining a first distance of the first vector,
    creating a second vector between a second voxel point in the lumen and a second voxel in the LNRC, wherein the second voxel point in the lumen is different then the first voxel in the lumen and the second voxel in the LRNC is different then the second voxel in the LRNC,
    determining a second distance of the second vector, and
    assigning the minimum distance to the smallest of the first distance and the second distance.

2. The system of claim 1 wherein segmenting the medical imaging data further comprises segmenting the medical imaging data into an outer wall boundary.

3. The system of claim 2 further wherein the analyzer module is configured to partition a lumen and an outer wall based on the segmented lumen boundary and outer wall boundary into one or more vessel boundaries.

4. The system of claim 3 wherein the biological properties include calcified regions, LRNC regions, intra-plaque regions, matrix regions, or any combination thereof.

5. A method for a hierarchical analytics framework, the method comprising:
    utilizing a first set of machine learned algorithms to identify and quantify a set of biological properties utilizing medical imaging data, wherein the biological properties include LRNC regions of a blood vessel, wherein the medical imaging data is computer tomography (CT) data; and
    segmenting the medical imaging data based on the quantified biological properties to determine a lumen boundary; and
    determining a cap thickness based on a minimum distance between the lumen boundary and LRNC regions, wherein the determining the minimum distance between the lumen boundary and the LRNC regions comprises:
    creating first vector between a first voxel in the lumen and first voxel in the LNRC,
    determining a first distance of the first vector,
    creating a second vector between a second voxel point in the lumen and a second voxel in the LNRC, wherein the second voxel point in the lumen is different then the first voxel in the lumen and the second voxel in the LRNC is different then the second voxel in the LRNC, determining a second distance of the second vector, and assigning the minimum distance to the smallest of the first distance and the second distance.

6. The method of claim 5 wherein segmenting the medical imaging data further comprises segmenting the medical imaging data into an outer wall boundary.

7. The method of claim 6 further wherein the analyzer module is configured to partition a lumen and an outer wall based on the segmented lumen boundary and outer wall boundary into one or more vessel boundaries.

8. The method of claim 7 wherein the biological properties include calcified regions, LRNC regions, intra-plaque regions, matrix regions, or any combination thereof.

* * * * *

UNITED STATES PATENT AND TRADEMARK OFFICE
CERTIFICATE OF CORRECTION

| | | |
|---|---|---|
| PATENT NO. | : 11,508,063 B2 | Page 1 of 1 |
| APPLICATION NO. | : 16/984640 | |
| DATED | : November 22, 2022 | |
| INVENTOR(S) | : Andrew J. Buckler | |

It is certified that error appears in the above-identified patent and that said Letters Patent is hereby corrected as shown below:

In the Specification

In Column 1, Line 12, insert the following:
--GOVERNMENT RIGHTS IN THE INVENTION
This invention was in part made with government support under National Institute of Health SBIR Award R44 HL126224 awarded by the National Institute of Health. The government may have certain rights in the invention.--

Signed and Sealed this
Twenty-fourth Day of January, 2023

Katherine Kelly Vidal
*Director of the United States Patent and Trademark Office*